United States Patent [19]

Carson et al.

[11] Patent Number: 4,507,498

[45] Date of Patent: Mar. 26, 1985

[54] PHENOXYCARBOXYLIC ACIDS

[75] Inventors: Matthew Carson, Nutley; Ronald A. LeMahieu, North Caldwell; William C. Nason, Mountain Lakes, all of N.J.

[73] Assignee: Hoffmann-La Roche Inc., Nutley, N.J.

[21] Appl. No.: 460,719

[22] Filed: Jan. 24, 1983

Related U.S. Application Data

[63] Continuation-in-part of Ser. No. 366,896, Apr. 9, 1982, abandoned.

[51] Int. Cl.³ .................. C07C 69/76; C07C 65/40
[52] U.S. Cl. .................................. 562/463; 560/53
[58] Field of Search .................. 560/53; 562/463; 424/308, 317

[56] References Cited

FOREIGN PATENT DOCUMENTS 0028063 5/1981 European Pat. Off. .
2058785 4/1981 United Kingdom .

*Primary Examiner*—Paul J. Killos
*Attorney, Agent, or Firm*—Jon S. Saxe; Bernard S. Leon; Matthew Boxer

[57] ABSTRACT

Phenoxycarboxylic acids of the formula

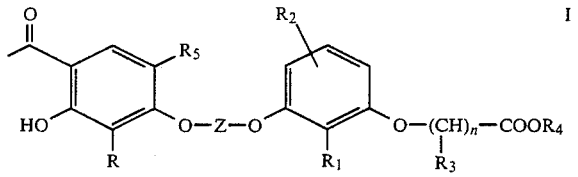

wherein R, $R_1$, $R_2$, $R_3$, $R_4$, $R_5$, Z and n are as hereinafter set forth, are as described. The compounds of formula I are antagonists of slow reacting substance of anaphylaxis (SRS-A), which renders them useful as agents for the treatment of allergic conditions.

15 Claims, No Drawings

PHENOXYCARBOXYLIC ACIDS

RELATED APPLICATIONS

This application is a continuation-in-part of application Ser. No. 366,896, filed Apr. 9, 1982 abandoned.

BRIEF SUMMARY OF THE INVENTION

The invention relates to compounds of the formula

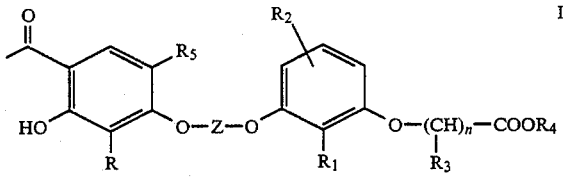

wherein R is hydrogen or lower alkyl, $R_1$ is hydrogen or lower alkyl, $R_2$ is lower alkanoyl, $R_3$ is hydrogen or methyl, $R_4$ is hydrogen or lower alkyl, $R_5$ is hydrogen, halogen, lower alkyl or lower alkanoyl, Z is lower alkylene, 2-hydroxypropylene or $-(CH_2)_s-[O(CH_2)_s]_t-$, wherein s is the integer 2, 3 or 4, t is the integer 1, 2 or 3, and n is an integer from 1 to 7, or, when $R_4$ is hydrogen,
salts thereof with pharmaceutically accetable bases. The compounds of formula I are useful as agents for the treatment of allergic conditions.

In another aspect, the invention relates to intermediates of the formulas

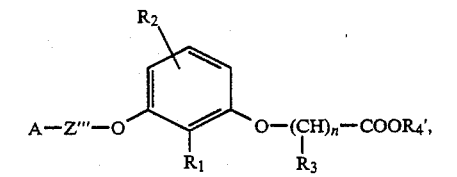

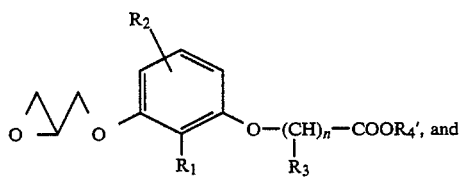

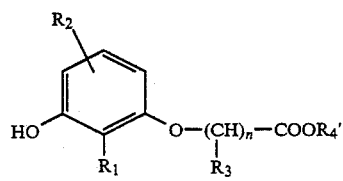

wherein $R_1$, $R_2$, $R_3$, $R_4'$, $Z'''$, A and n are as herein described.

DETAILED DESCRIPTION OF THE INVENTION

As used herein, the term "lower alkyl" denotes a straight or branched chain saturated hydrocarbon containing 1 to 7 carbon atoms, for example, methyl, ethyl, propyl, isopropyl, butyl, t-butyl, neopentyl, pentyl, heptyl and the like. The term "lower alkylene" denotes a hydrocarbon radical of 2 to 5 carbon atoms, preferably of 3 to 5 carbon atoms, such as ethylene, propylene, butylene and pentylene. The term "lower alkanoyl" denotes an alkanoyl group derived from an aliphatic carboxylic acid of 1 to 7 carbon atoms, for example, formyl, acetyl, propionyl, butyryl and the like. The term "halogen" denotes all the halogens, that is, bromine, chlorine, fluorine and iodine.

The invention relates to compounds of the formula

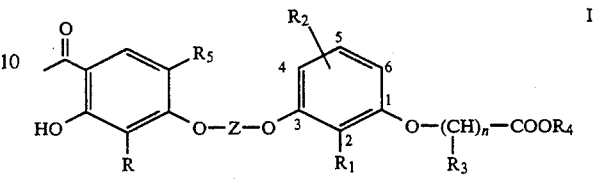

wherein R is hydrogen or lower alkyl, $R_1$ is hydrogen or lower alkyl, $R_2$ is lower alkanoyl, $R_3$ is hydrogen or methyl, $R_4$ is hydrogen or lower alkyl, $R_5$ is hydrogen, halogen, lower alkyl or lower alkanoyl, Z is lower alkylene, 2-hydroxypropylene or $-(CH_2)_s-[O(CH_2)_s]_t-$ wherein s is the integer 2, 3 or 4, t is the integer 1,2 or 3, and n is an integer from 1 to 7,
and, when $R_4$ is hydrogen, salts thereof with pharmaceutically acceptable bases, which can be prepared as hereinafter described.

An interesting group of compounds of the invention are compounds of the formula

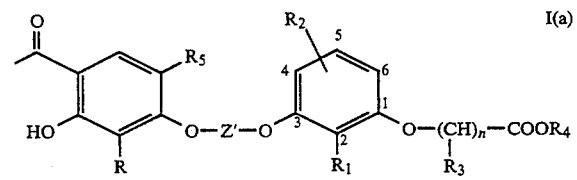

wherein R is hydrogen or lower alkyl, $R_1$ is hydrogen or lower alkyl, $R_2$ is lower alkanoyl, $R_3$ is hydrogen or methyl, $R_4$ is hydrogen or lower alkyl, $R_5$ is hydrogen, halogen, lower alkyl or lower alkanoyl, $Z'$ is lower alkylene or 2-hydroxypropylene, and n is an integer from 1 to 7, or, when $R_4$ is hydrogen, a salt thereof with a pharmaceutically acceptable base.

Another interesting group of compounds of the invention are compounds of the formula

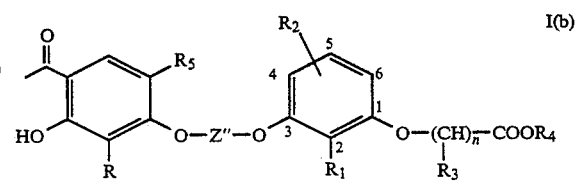

wherein R is hydrogen or lower alkyl, $R_1$ is hydrogen or lower alkyl, $R_2$ is lower alkanoyl, $R_3$ is hydrogen or methyl, $R_4$ is hydrogen or lower alkyl, $R_5$ is hydrogen, halogen, lower alkyl or lower alkanoyl, $Z''$ is $-(CH_2)_s-[-O(CH_2)_s-]_t-$, wherein s is the integer 2, 3 or 4, t is the integer 1, 2 or 3, and n is an integer from 1 to 7, or, when $R_4$ is hydrogen, a salt thereof with a pharmaceutically acceptable base.

Preferred compounds of formula Ia are those wherein $R_2$ is in the 4-position, and $R_4$ is hydrogen. Of these, the more preferred compounds are those wherein $R_3$ and $R_5$ are hydrogen, $Z'$ is propylene or pentylene, R and $R_1$ are lower alkyl, and n is 1 or 3. Still more preferred compounds of formula Ia are those wherein R₃ and R₅ are hydrogen, Z' is pentylene, R and R₁ are propyl, R₂ is acetyl in the 4-position, R₄ is hydrogen and n is 1 or 3.

Preferred compounds of formula Ib are those wherein R₂ is in the 4-position, and R₄ is hydrogen. Of these, the more preferred compounds are those wherein R and R₁ are lower alkyl, R₃ and R₅ are hydrogen, and n is 1 or 3. Still more preferred compounds of formula Ib are those wherein R₃ and R₅ are hydrogen, R and R₁ are propyl, R₂ is acetyl in the 4-position, R₄ is hydrogen, n is 1 or 3 and s is 2 or 3.

Most preferred compounds of formula I are:

[4-acetyl-3-[3-(4-acetyl-3-hydroxy-2-propylphenoxy)-propoxy]-2-propylphenoxy]acetic acid;

racemic [4-acetyl-3-[3-(4-acetyl-3-hydroxy-2-propylphenoxy)-2-hydroxypropoxy]-2-propylphenoxy]acetic acid;

4-[4-acetyl-3-[3-(4-acetyl-3-hydroxy-2-propylphenoxy)-propoxy]-2-propylphenoxy]butanoic acid;

4-[4-acetyl-3-[3-[3-(4-acetyl-3-hydroxy-2-propylphenoxy)propoxy]propoxy]-2-propylphenoxy]-butanoic acid;

[4-acetyl-3-[2-[2-[2-[2-(4-acetyl-3-hydroxy-2-propylphenoxy)ethoxy]ethoxy]ethoxy]ethoxy]-2-propylphenoxy]acetic acid;

[4-acetyl-3-[2-[2-[2-(4-acetyl-3-hydroxy-2-propylphenoxy)ethoxy]ethoxy]ethoxy]-2-propylphenoxy]acetic acid;

[4-acetyl-3-[2-[2-(4-acetyl-3-hydroxy-2-propylphenoxy)ethoxy]ethoxy]-2-propylphenoxy]acetic acid;

4-[4-acetyl-3-[[5-(4-acetyl-3-hydroxy-2-propylphenoxy)pentyl]oxy]-2-propylphenoxy]butanoic acid; and

[4-acetyl-3-[5-(4-acetyl-3-hydroxy-2-propylphenoxy)-pentyloxy]-2-propylphenoxy]acetic acid.

Exemplary of other compounds of formula I are:

[4-acetyl-3-[5-(4-acetyl-3-hydroxy-2-propylphenoxy)-pentyloxy]-2-propylphenoxy]-acetic acid;

[4-acetyl-3-[3-(4-acetyl-3-hydroxy-2-propylphenoxy)-propoxy]phenoxy]acetic acid;

[6-acetyl-3-[3-(4-acetyl-3-hydroxy-2-propylphenoxy)-propoxy]-2-propylphenoxy]acetic acid;

racemic-[4-acetyl-3-[3-(4-acetyl-3-hydroxy-2-propylphenoxy)propoxy]-2-propylphenoxy]methylacetic acid;

[4-acetyl-3-[2-[2-(4-acetyl-3-hydroxy-2-propylphenoxy)ethoxy]ethoxy]-2-propylphenoxy]acetic acid;

[4-acetyl-3-[3-(4-acetyl-3-hydroxy-6-iodo-2-propylphenoxy)propoxy]-2-propylphenoxy]acetic acid;

[4-acetyl-3-[3-(4,6-diacetyl-3-hydroxy-2-propylphenoxy)propoxy]-2-methylphenoxy]acetic acid;

[4-acetyl-3-[3-(4-acetyl-3-hydroxy-2-methylphenoxy)-propoxy]-2-methyl phenoxy]acetic acid;

[4-acetyl-3-[3-(4-acetyl-6-chloro-3-hydroxy-2-propylphenoxy)propoxy]-2-propyl phenoxy]acetic acid;

[4-acetyl-3-[3-(4-acetyl-2,6-dipropyl-3-hydroxyphenoxy)propoxy]-2-propyl phenoxy]acetic acid;

[4-acetyl-3-[3-(4-acetyl-3-hydroxy-2-methylphenoxy)-propoxy]-2-propylphenoxy]acetic acid;

4-[4-acetyl-3-[3-(4-acetyl-6-chloro-3-hydroxy-2-propylphenoxy)propoxy]2-propylphenoxy]butanoic acid;

4-[4-acetyl-3-[3-(4,6-diacetyl-3-hydroxy-2-propylphenoxy)propoxy]2-propylphenoxy]butanoic acid;

4-[4-acetyl-3-[3-(4-acetyl-3-hydroxy-2-propylphenoxy)-2-hydroxypropoxy]-2-propylphenoxy]butanoic acid.

3-[4-acetyl-3-[3-[3-(4-acetyl-3-hydroxy-2-propylphenoxy)propoxy]propoxy]-2-propylphenoxy]-propanoic acid;

5-[4-acetyl-3-[3-[3-(4-acetyl-3-hydroxy-2-propylphenoxy)propoxy]propoxy]-2-propylphenoxy]pentanoic acid;

3-[4-acetyl-3-[2-[2-[2-(4-acetyl-3-hydroxy-2-propylphenoxy)ethoxy]ethoxy]ethoxy]-2-propylphenoxy]-propanoic acid;

5-[4-acetyl-3-[2-[2-[2-(4-acetyl-3-hydroxy-2-propylphenoxy)ethoxy]ethoxy]ethoxy]-2-propylphenoxy]-pentanoic acid;

3-[4-acetyl-3-[2-[2-[2-[2-(4-acetyl-3-hydroxy-2-propylphenoxy)ethoxy]ethoxy]ethoxy]ethoxy]-2-propylphenoxy]propanoic acid; and the like.

The compounds of formula I of the invention can be prepared as hereinafter described in Reaction Schemes I to IV which follow:

Reaction Scheme I

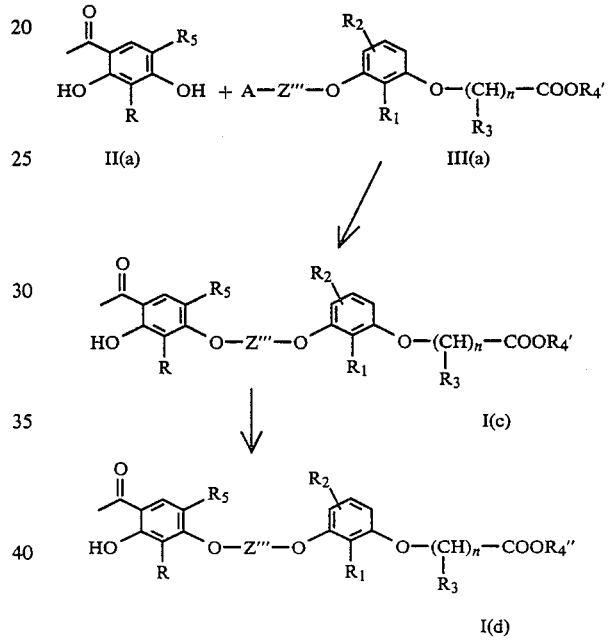

wherein R, R₁, R₂, R₃, R₅ and n are as previously described, and Z''' is lower alkylene or —(CH₂)ₛ—[O(CH₂)ₜ]ₜ, wherein s is the integer 2, 3 or 4, t is the integer 1, 2 or 3, R₄' is lower alkyl, R₄'' is hydrogen, and A is halogen or methylsulfonyloxy.

In Reaction Scheme I, the reaction of a compound of formula II(a) with a compound of formula III(a) to yield a compound of formula I(c) is carried out under anhydrous conditions in an inert solvent, for example, acetone, methylethyl ketone, diethyl ketone, dimethylformamide or the like, at the reflux temperature of the reaction mixture, in dimethylformamide, preferably at a temperature in the range of 70°–100° C., and in the presence of an acid acceptor, for example, potassium carbonate or the like. The preferred solvent is a mixture of acetone and dimethylformamide. In a compound of formula III(a), A preferably is bromine and the reaction is sometimes carried out in the presence of a catalyst, for example, potassium iodide or the like. The resulting compound of formula I(c) can be recovered utilizing conventional methods, for example, crystallization, chromatography or the like.

A resulting compound of formula I(c) can be converted to a compound of formula I(d) by hydrolysis which is carried out with an alkali metal hydroxide, for example, sodium hydroxide, potassium hydroxide or the like, in a mixture of water and a water miscible alcohol, for example, methanol, ethanol or the like, at a temperature in the range of from about room temperature to the reflux temperature. The resulting compound of formula I(d) can be recovered utilizing conventional methods, for example, crystallization, chromatography or the like.

Reaction Scheme II

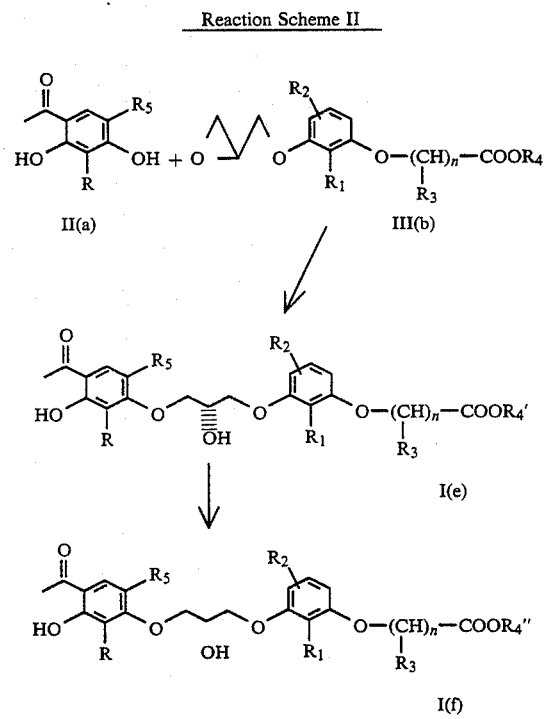

wherein R, $R_1$, $R_2$, $R_3$, $R_5$ and n are as previously described, $R_4'$ is lower alkyl and $R_4''$ is hydrogen.

In Reaction Scheme II, the reaction of a compound of formula II(a) with a compound of formula III(b) to yield a compound of formula I(e) is carried out at an elevated temperature, which usually is the reflux temperature of the reaction mixture, in an inert solvent, for example, dimethylformamide, dioxane or the like, and in the presence of a suitable catalyst, for example, benzyltrimethylammonium hydroxide or the like. Suitably, the reaction can be carried out by refluxing with t-amyl alcohol in the presence of sodium t-amyloxide. The resulting compound of formula I(e) can be recovered utilizing conventional methods, for example, crystallization, chromatography or the like.

A resulting compound of formula I(e) can be converted to a compound of formula I(f) by hydrolysis as described in Reaction Scheme I for the conversion of a compound of formula I(c) to a compound of formula I(d). The resulting compound of formula I(f) can be recovered utilizing conventional methods, for example, crystallization, chromatography or the like.

Reaction Scheme III

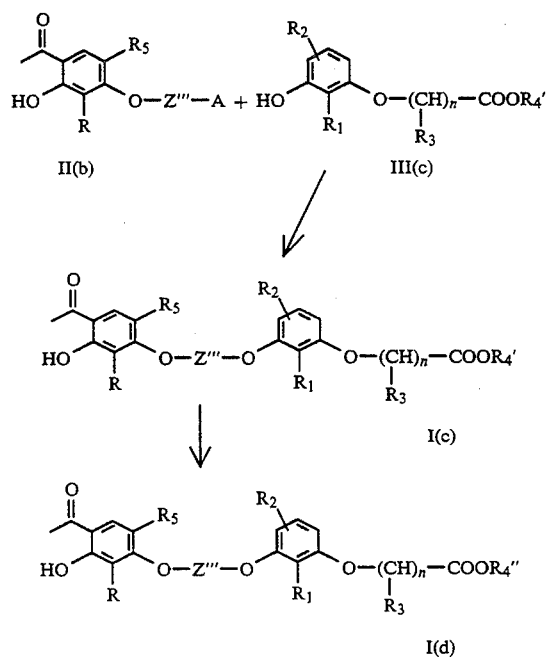

wherein A, R, $R_1$, $R_2$, $R_3$, $R_5$ and n are as previously described, $Z'''$ is lower alkylene or $—(CH_2)_s—[—O(CH_2)_s—]_t—$, wherein s is the integer 2, 3 or 4, t is the integer 1, 2 or 3, $R_4'$ is lower alkyl and $R_4''$ is hydrogen.

In Reaction Scheme III, the reaction of a compound of formula II(b) with a compound of formula III(c) to yield a compound of formula I(c) is carried out utilizing the reaction conditions already described in Reaction Scheme I for the reaction of a compound of formula II(a) and a compound of formula III(a). The resulting compound of formula I(c) can be recovered utilizing conventional methods, for example, crystallization, chromatography or the like.

The conditions for the conversion of a compound of formula I(c) to a compound of formula I(d) by hydrolysis are described in Reaction Scheme I. The resulting compound of formula I(d) can be recovered utilizing conventional methods, for example, crystallization, chromatography or the like.

Reaction Scheme IV

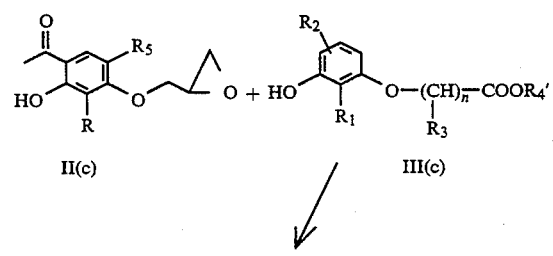

-continued
Reaction Scheme IV

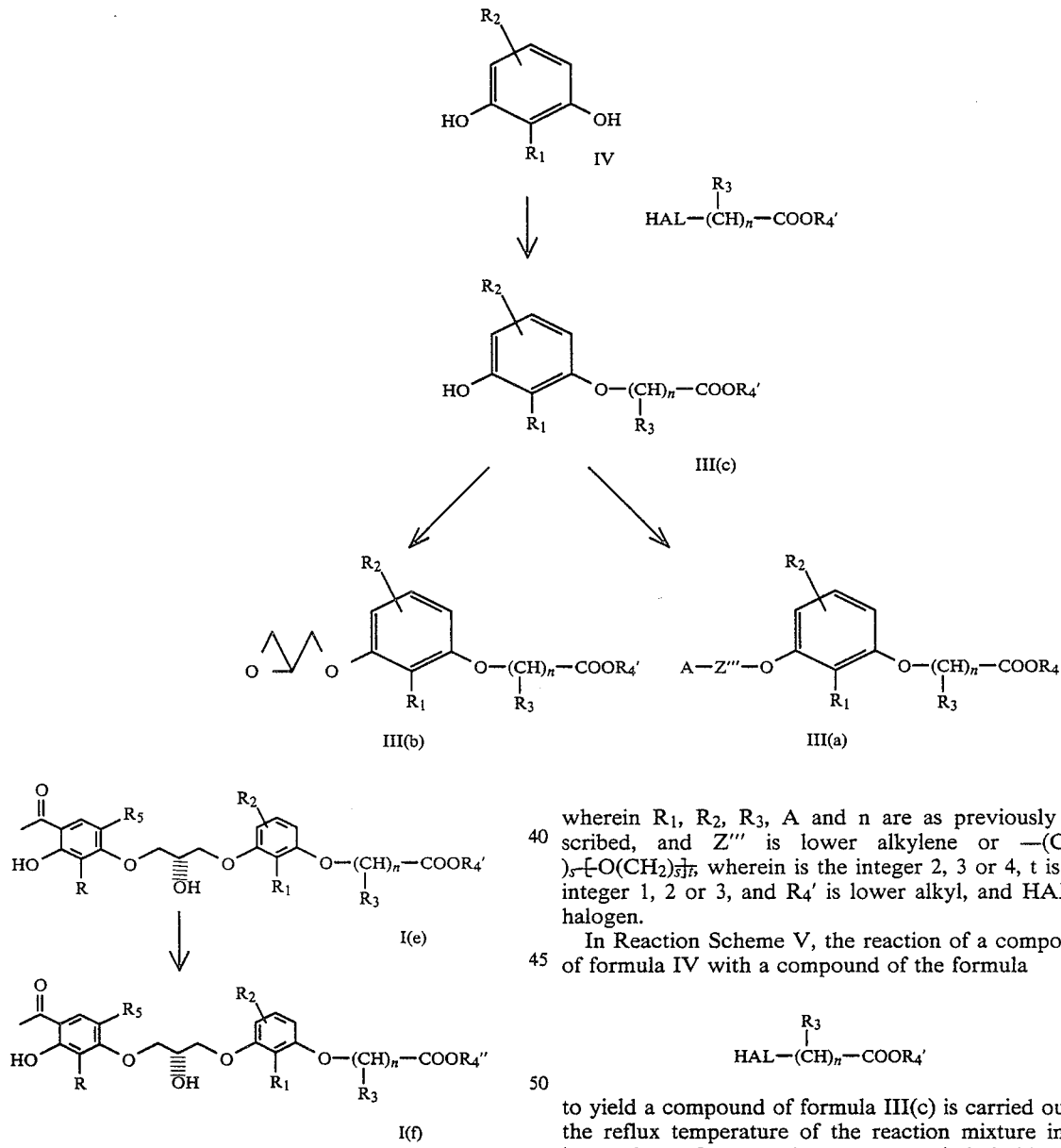

III(c)

III(b)              III(a)

I(e)

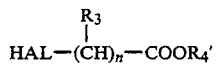

I(f)

wherein R, $R_1$, $R_2$, $R_3$, $R_5$ and n are as previously described, $R_4'$ is lower alkyl and $R_4''$ is hydrogen.

In Reaction Scheme IV, the reaction of a compound of formula II(c) with a compound of formula III(c) to yield a compound of formula I(e) is carried out under the reaction conditions set out in Reaction Scheme II for the reaction of a compound of formula II(a) and a compound of formula III(b). The resulting compound of formula I(e) can be recovered utilizing conventional methods, for example, crystallization, chromatography or the like.

The conversion of a compound of formula I(e) to a compound of formula I(f) is carried out by hydrolysis as set out in Reaction Scheme II also for the conversion of a compound of formula I(e) to a compound of formula I(f). The resulting compound of formula I(f) can be recovered utilizing conventional methods, for example, crystallization, chromatography or the like.

Reaction Scheme V wherein $R_1$, $R_2$, $R_3$, A and n are as previously described, and Z''' is lower alkylene or —(CH$_2$-)$_s$-[-O(CH$_2$)$_s$]$_t$, wherein s is the integer 2, 3 or 4, t is the integer 1, 2 or 3, and $R_4'$ is lower alkyl, and HAL is halogen.

In Reaction Scheme V, the reaction of a compound of formula IV with a compound of the formula $$\text{HAL}-(\overset{R_3}{\underset{|}{\text{CH}}})_n-\text{COOR}_4'$$

to yield a compound of formula III(c) is carried out at the reflux temperature of the reaction mixture in an inert solvent, for example, acetone, methylethyl ketone, diethyl ketone or the like, in the presence of an acid acceptor, for example, potassium carbonate, sodium carbonate or the like. This reaction can also be carried out utilizing a base, for example, sodium hydride or the like, under anhydrous conditions in a solvent, for example, dimethylformamide, tetrahydrofuran, dioxane or the like, at a temperature in the range of from about 25° C. to about 70° C. The resulting compound of formula III(c) can be recovered utilizing conventional methods, for example, crystallization, chromatography or the like.

The conversion of a compound of formula III(c) to a compound of formula III(b) is conveniently carried out by reacting a compound of formula III(c) with epibromohydrin or epichlorohydrin in the presence of potassium carbonate, sodium carbonate or the like, in a solvent, for example, acetone, methylethyl ketone, dimethylformamide or the like, at a temperature in the range of from about 55° C. to about 80° C., and in the presence of a catalytic amount of potassium iodide or the like. The resulting compound of formula III(b) can be recovered utilizing conventional methods, for example, crystallization, chromatography or the like.

The conversion of a compound of formula III(c) to a compound of formula III(a) is conveniently carried out by reacting a compound of formula III(c) with a dihaloalkane, for example, a dibromoalkane such as 1,3-dibromopropane, a dimesylate such as diethyleneglycol dimesylate or a dibromoether such as 1,11-dibromo-3,6,9-trioxaundecane in the presence of potassium carbonate, sodium carbonate or the like, and in a solvent, for example, acetone, methylethyl ketone or mixtures of these with dimethylformamide or the like. The reaction is carried out at the reflux temperature of the reaction mixture. The resulting compound of formula III(a) can be recovered utilizing conventional methods, for example, crystallization, chromatography or the like.

The starting materials of the formula

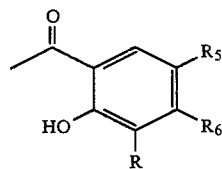

II wherein R<sub>6</sub> is hydroxy, A

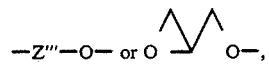

and A, Z''',
R and R<sub>5</sub> are as previously described,
are known compounds or can be prepared according to known procedures. Exemplary of such compounds are:
1-(2,4-dihydroxy-3-propylphenyl)ethanone;
1-(2,4-dihydroxy-3-methylphenyl)ethanone;
1-(2,4-dihydroxy-3-ethylphenyl)ethanone;
1-(2,4-dihydroxy-3,5-dipropylphenyl)ethanone;
1-(5-chloro-2,4-dihydroxy-3-propylphenyl)ethanone;
1-(5-acetyl-2,4-dihydroxy-3-propylphenyl)ethanone;
1-[4-(3-bromopropoxy)-2-hydroxy-3-propylphenyl]ethanone;
1-[4-(5-bromopentyloxy)-2-hydroxy-3-propylphenyl]ethanone;
1-[4-(3-bromopropoxy)-2-hydroxy-3-methylphenyl]ethanone;
1-[4-(3-bromopropoxy)-2-hydroxy-3-ethylphenyl]ethanone;
1-[4-(3-bromopropoxy)-3,5-dipropyl-2-hydroxyphenyl]ethanone;
1-[4-(3-bromopropoxy)-5-chloro-2-hydroxy-3-propylphenyl]ethanone;
1-[5-acetyl-4-(3-bromopropoxy)-2-hydroxy-3-propylphenyl]ethanone;
1-[2-hydroxy-4-(oxiranylmethoxy)-3-propylphenyl]ethanone;
1-[2-hydroxy-4-(oxiranylmethoxy)-3-methylphenyl]ethanone;
1-[2-hydroxy-5-iodo-4-(oxiranylmethoxy)-3-propylphenyl]ethanone;
1-[5-acetyl-2-hydroxy-4-(oxiranylmethoxy)-3-propylphenyl]ethanone;
1-[4-[2-(2-bromoethoxy)ethoxy]-2-hydroxy-3-propylphenyl]ethanone;
1-[4-[2-[2-(2-bromoethoxy)ethoxy]ethoxy]-2-hydroxy-3-propylphenyl]ethanone;
1-[4-[2-[2-[2-(2-bromoethoxy)ethoxy]ethoxy]-2-hydroxy-3-propylphenyl]ethanone;
1-[4-[3-(3-bromopropoxy)propoxy]-2-hydroxy-3-propylphenyl]ethanone; and the like.

The starting materials of the formula

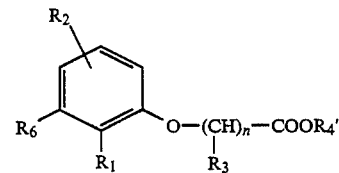

III wherein R<sub>6</sub> is hydroxy, A

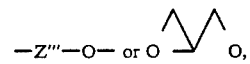

and A, Z''',
R<sub>1</sub>, R<sub>2</sub>, R<sub>3</sub>, R<sub>4</sub>' and n are as previously described, can be prepared according to Reaction Scheme V. Exemplary of such compounds are:
(4-acetyl-3-hydroxy-2-propylphenoxy)acetic acid ethyl ester;
(4-acetyl-3-hydroxy-2-propylphenoxy)acetic acid methyl ester;
[4-acetyl-3-(3-bromopropoxy)-2-propylphenoxy]acetic acid ethyl ester;
[4-acetyl-3-(3-bromopropoxy)-2-propylphenoxy]acetic acid methyl ester;
[4-acetyl-3-(oxiranylmethoxy)-2-propylphenoxy]acetic acid ethyl ester;
[4-acetyl-3-(oxiranylmethoxy)-2-propylphenoxy]acetic acid methyl ester;
[6-acetyl-3-(3-bromopropoxy)-2-propylphenoxy]acetic acid ethyl ester;
[6-acetyl-3-(oxiranylmethoxy)-2-propylphenoxy]acetic acid ethyl ester;
[4-acetyl-3-(5-bromopentyloxy)-2-propylphenoxy]acetic acid ethyl ester;
(4-acetyl-3-hydroxyphenoxy)acetic acid ethyl ester;
[4-acetyl-3-(3-bromopropoxy)-phenoxy]acetic acid ethyl ester;
4-(4-acetyl-3-hydroxy-2-propylphenoxy)butanoic acid ethyl ester;
4-[4-acetyl-3-(3-bromopropoxy)-2-propylphenoxy]-butanoic acid ethyl ester;
racemic-(4-acetyl-3-hydroxy-2-propylphenoxy)-alpha-methylacetic acid ethyl ester;
racemic-[4-acetyl-3-(3-bromopropoxy)-2-propylphenoxy]-alpha-methyl acetic acid ethyl ester;
[4-acetyl-3-[2-(2-chloroethoxy)ethoxy]-2-propylphenoxy]acetic acid ethyl ester;
(4-acetyl-3-hydroxy-2-methylphenoxy)acetic acid methyl ester;
[4-acetyl-3-(3-bromopropoxy)-2-methylphenoxy]acetic acid methyl ester;
[4-acetyl-3-oxiranylmethoxy)-2-methylphenoxy]acetic acid methyl ester;

[4-acetyl-3-[2-[2-[2-[(methylsulfonyl)oxy]ethoxy]ethoxy]ethoxy]-2-propylphenoxy]acetic acid ethyl ester;
[4-acetyl-3-[2-[2-[2-(2-bromoethoxy)ethoxy]ethoxy]ethoxy]-2-propylphenoxy]acetic acid ethyl ester;
[4-acetyl-3-[3-(3-bromopropoxy)propoxy]-2-propylphenoxy]butanoic acid ethyl ester; and the like.

This invention also relates to the pharmaceutically acceptable salts of the phenoxycarboxylic acid derivatives of formula I, wherein $R_4$ is hydrogen. Said salts can be prepared by reacting an acid of formula I with a base having a non-toxic, pharmacologically and pharmaceutically acceptable cation. In general, any base which will form salt with a carboxylic acid and whose pharmacological properties will not cause an adverse physiological effect when ingested by a warmed blooded animal is considered as being within the scope of this invention. Suitable bases thus include, for example, the alkali metal and alkaline earth metal hydroxides, carbonates, for example, sodium hydroxide, potassium hydroxide, calcium hydroxide, potassium carbonate and the like, ammonia, primary, secondary and tertiary amines, such as monoalkylamines, dialkylamines, trialkylamines, nitrogen containing heterocyclic amines, for example, piperidine, amino acids such as lysine, and the like. The pharmaceutically acceptable salts thus produced are the functional equivalent of the corresponding phenoxycarboxylic acids of formula I and one skilled in the art will appreciate that, to the extent that the salts of the invention are useful in therapy, the variety of salts encompassed by this invention are limited only by the criterion that the bases employed in forming the salts be both non-toxic and physiologically acceptable.

The compounds of formula I of the invention are useful in the treatment of disorders in which slow reacting substance of anaphylaxis (SRS-A) is a mediator. The compounds of formula I are therefore useful in the treatment of allergic disorders which include skin afflictions, hay fever, chronic bronchitis, obstructive airways diseases such as asthma, allergic conditions of the eye, and allergic conditions of the gastro-intestinal tract, such as food allergies.

The useful antiallergic activity of the compounds of formula I is demonstrated in vitro and in warm-blooded animals utilizing standard procedures. Exemplary of such procedures are:

(a) Guinea Pig Ileum, In Vitro

The guinea pig ileum bioassay system has been described by Orange and Austen, Adv. Immunol. 10: 105–144 (1969). A 1.5 cm segment is removed from animals weighing 300–400 g and suspended in an organ bath containing 10 ml of Tyrodes solution with $10^{-6}$M atropine sulfate and $10^{-6}$M pyrilamine maleate. The bath is maintained at 37° C. and aerated with a mixture of 95% oxygen and 5% carbon dioxide. The SRS-A utilized in this screen is obtained by challenging chopped lung fragments from actively sensitized guinea pigs with egg albumin, in vitro. A dose-response curve to SRS-A challenge is established for the ileum. The dose of SRS-A which gives 50% of the maximal contraction ($EC_{50}$) is then used for subsequent challenge. The drug concentration which inhibits, by 50%, the SRS-A-induced constriction of the guinea pig ileum is determined. In this bioassay system the standard SRS-A antagonist, 7-[3-(4-acetyl-3-hydroxy-2-propylphenoxy)-2-hydroxypropoxy]-4-oxo-8-propyl-4H-1-benzopyran-2-carboxylic cid, has an $IC_{50}$ of $3.5 \times 10^{-8}$M.

(b) Guinea Pig Bronchoconstriction, In Vivo

Male guinea pigs (Hostley strain) weighing 300 to 450 grams are anesthetized with urethane (2 g/kg) intraperitoneally and a polyethylene cannula is inserted into the jugular vein for intravenous drug administration. Tracheal pressure is recorded from a cannula inserted in the trachea and connected to a Statham pressure transducer. Respiration is paralyzed with succinyl choline (1.2 mg/kg, i.v.) and the animals are mechanically respirated (Howard rodent respirator) at 40 breaths/minute and 2.5 cc tidal volume. Two minutes thereafter, propranolol (0.1 mg/kg, i.v.) is administered. Five minutes later, the animals are pretreated intravenously for 30 seconds (at 10 mg/kg) with test drug or control vehicle. The animals are subsequently challenged with a maximally constrictory dose of leukotriene $E_4$ also administered intravenously. The change (cm $H_2O$) between pre and peak ventilatory pressure readings is averaged for three control animals and five drug treated animals. The percent inhibition is calculated from the following formula:

$$\frac{\text{Control} - \text{Drug Treated}}{\text{Control}} \times 100.$$

For determination of oral activity, spontaneously breathing animals are pretreated orally for 2 hours (at 100 mg/kg) prior to challenge with leukotriene $E_4$. 7-[3-(4-Acetyl-3-hydroxy-2-propylphenoxy)-2-hydroxypropoxy]-4-oxo-8-propyl-4H-1-benzopyran-2-carboxylic acid elicits a 98% inhibition at 10 mg/kg, i.v., but is orally inactive in this test.

(c) Guinea Pig Bronchoconstriction, In Vivo (Aerosol)

Male guinea pigs (Hartley strain) weighing 300 to 500 g are anesthetized with urethane (2 g/kg) intraperitoneally and a polyethylene cannula is inserted into the jugular vein for drug administration. Tracheal pressure is recorded from a cannula inserted in the trachea and connected to a Statham pressure transducer. After surgical preparation of the animals, a period of time is allowed for pulmonary functions to stabilize. The test compound is administered according to the following protocol. Propranolol (0.1 mg/kg) is administered intravenously while the animals breathed spontaneously. Five minutes thereafter, the animals are exposed for a five minute period to a 1% (w/v) aerosol solution of test compound (adjusted to an alkaline pH where necessary for drug solubilization) or to distilled water of the appropriate pH (for control purposes). A Monaghan (Model 750) ultrasonic nebulizer is used to administer all test compounds by inhalation. The nebulizer ultrasonic frequency is adjusted to produce particles in the 1–8$\mu$ diameter range (average 3$\mu$). Aqueous solutions are prepared fresh and introduced into the chamber of the nebulizer. The output of the nebulizer is made available to the animal by directing a bias flow of aerosol through a y tube connected to the tracheal cannula. At the end of the exposure period, the animals are paralyzed with succinylcholine (1.2 mg/kg, i.v.) and mechanically respirated (Harvard rodent respirator) at 40 breaths/minute and 2.5 cc tidal volume. Animals are then challenged with a maximum constrictory dose of leukotriene $E_4$ delivered intravenously 30 seconds after administration of the succinylcholine.

The change (cm $H_2O$) between pre and peak ventilatory pressure readings is averaged for three control animals and five drug treated animals. The percent inhibition is calculated from the following formula:

$$\frac{\text{Control} - \text{Drug Treated}}{\text{control}} \times 100$$

When various drug concentrations are tested, the percent inhibition at each concentration is plotted as log concentration (abscissa) versus percent inhibition (ordinate) and the $IC_{50}$ is determined from linear regression analysis.

In order to determine the duration of action (doa), the animals are prepared as described above, except that the time between aerosol exposure and challenge with $LTE_4$ is varied. All compounds are administered at a concentration of 1%. Duration of action is calculated from plots of time (abscissa) versus % inhibition (ordinate). The duration of action is defined as the time for the % inhibition to fall below 40%.

When the compounds of formula I, listed hereinafter in Table I, were utilized in the test procedures described above, the result set out in Table I were obtained:

inhibitors, methyl xanthines, $B_2$ agonists or antiasthmatic steroids such as prednisone and prednisolone, orally, parenterally, rectally or by inhalation, for example, in the form of an aerosol, micropulverized powder or nebulized solution. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or water or combinations of miscible solvents, and mixed with a pharmaceutically acceptable propellant. Such aerosol compositions are packaged for

TABLE I

| Test Compound | Guinea Pig Ileum In Vitro $IC_{50}(M)$ | Guinea Pig Bronchoconstriction, In Vivo % I | | Guinea Pig Bronchoconstriction, In Vivo Aerosol $IC_{50}$ (%) | Aerosol Duration of Action (min.) | $LD_{50}$ |
|---|---|---|---|---|---|---|
| | | 10 mg/kg I.V. | 100 mg/kg P.O. | | | |
| [4-Acetyl-3-[3-(4-acetyl-3-hydroxy-2-propylphenoxy)propoxy]-2-propylphenoxy]acetic acid | $2 \times 10^{-6}$ | 95 | 52 | $0.07^{(a)}$ | 90 | 500 mg/kg p.o. 90 mg/kg i.p. |
| [4-Acetyl-3-[3-(4-acetyl-3-hydroxy-2-propylphenoxy)propoxy]-2-propylphenoxy]butanoic acid | $2 \times 10^{-7}$ | 97 | 81 | $0.44^{(a)}$ | | 770 mg/kg p.o. 650 mg/kg i.p. |
| racemic [4-Acetyl-3-[3-(4-acetyl-3-hydroxy-2-propylphenoxy)-2-hydroxypropoxy]-2-propylphenoxy]acetic acid | $1 \times 10^{-6}$ | 89 | 29 | $0.1^{(b)}$ | 72 | |
| 4-[4-acetyl-3-[3-[3-(4-acetyl-3-hydroxy-2-propylphenoxy)propoxy]propoxy]-2-propylphenoxy]butanoic acid | $2 \times 10^{-7}$ | 93 | 56 | 0.008 | 37 | |
| [4-acetyl-3-[2-[2-[2-(4-acetyl-3-hydroxy-2-propylphenoxy)ethoxy]ethoxy]ethoxy]-2-propylphenoxy]acetic acid | $3 \times 10^{-7}$ | 90 | | 0.04 | 73 | |
| [4-acetyl-3-[2-[2-[2-(4-acetyl-3-hydroxy-2-propylphenoxy)ethoxy]ethoxy]ethoxy]-2-propylphenoxy]acetic acid | $1 \times 10^{-6}$ | 85 | 4 | 0.04 | 42 | 650 mg/kg p.o. 120 mg/kg i.p. |
| [4-acetyl-3-[2-[2-(4-acetyl-3-hydroxy-2-propylphenoxy)ethoxy]ethoxy]-2-propylphenoxy]acetic acid | $2 \times 10^{-7}$ | 86 | 26 | 0.02 | 14 | 800 mg/kg p.o. 170 mg/kg i.p. |
| 4-[4-acetyl-3-[[5-(4-acetyl-3-hydroxy-2-propylphenoxy)pentyl]oxy]-2-propylphenoxy]butanoic acid | $1 \times 10^{-6}$ | 92 | 84 | 0.01 | 46 | |
| [4-acetyl-3-[5-(4-acetyl-3-hydroxy-2-propylphenoxy)pentyloxy]-2-propylphenoxy]acetic acid | $1 \times 10^{-7}$ | 91 | 51 | 0.02 | 55 | 900 mg/kg p.o. 140 mg/kg i.p. |

$^{(a)}IC_{50}$ was determined using % inhibition valves obtained 30 seconds after exposure to test drug.
$^{(b)}IC_{50}$ was determined using % inhibition valves obtained 15 minutes after exposure to test drug.

A compound of formula I or a salt thereof when $R_4$ is hydrogen, or a composition containing a therapeutically effective amount of a compound of formula I or a salt thereof, when $R_4$ is hydrogen, can be administered by methods well known in the art. Thus, a compound of formula I, or a salt thereof when $R_4$ is hydrogen, can be administered either singly or with other pharmaceutical agents, for example, antihistamines, mediator release use in a pressurized container fitted with an aerosol valve suitable for release of the pressurized composition. Preferably, the aerosol valve is a metered valve, that is one which on activation releases a predetermined effective dose of the aerosol composition.

In the practice of the invention, the dose of a compound of formula I or a salt thereof when $R_4$ is hydrogen to be administered and the frequency of administration will be dependent on the potency and duration of activity of the particular compound of formula I or salt to be administered and on the route of administration, as well as the severity of the condition, age of the mammal to be treated and the like. Doses of a compound of formula I or a salt thereof when $R_4$ is hydrogen contemplated for use in practicing the invention are in the range of from about 25 to about 1000 mg per day, preferably about 25 to about 250 mg either as a single dose or in divided doses.

The Examples which follow further illustrate the invention. All temperatures are in degrees centigrade, unless other wise stated.

EXAMPLE 1

Preparation of (4-acetyl-3-hydroxy-2-propylphenoxy)acetic acid ethyl ester

A mixture of 3.88 g of 1-(2,4-dihydroxy-3-propylphenyl)ethanone, 2.4 ml of ethyl bromoacetate and 4.0 g of anhydrous potassium carbonate in 50 ml of anhydrous acetone was stirred at reflux for 6 hours. The reaction mixture was filtered and the filtrate was concentrated in vacuo to an oil which was purified by chromatography on silica gel. Elution with 20% ethyl acetate-toluene gave 4.13 g, mp 51°–52°, (73% yield) of (4-acetyl-3-hydroxy-2-propylphenoxy)acetic acid ethyl ester.

EXAMPLE 2

Preparation of [4-acetyl-3-(3-bromopropoxy)-2-propylphenoxy]acetic acid ethyl ester A mixture of 4.13 g of (4-acetyl-3-hydroxy-2-propylphenoxy)acetic acid ethyl ester, 7.6 ml of 1,3-dibromopropane and 3.0 g of anhydrous potassium carbonate in 100 ml of anhydrous acetone was stirred at reflux for 73 hours. An additional 1.0 g of potassium carbonate was added and reflux was continued for 19 hours at which time 1.0 g of potassium carbonate was added. After 16 hours reflux, the reaction mixture was filtered and the filtrate was concentrated in vacuo. The crude product was chromatographed on 200 g of silica gel and eluted with 15% ethyl acetate-toluene to give 4.82 g of [4-acetyl-3-(3-bromopropoxy)-2-propylphenoxy]acetic acid ethyl ester.

EXAMPLE 3

Preparation of [4-acetyl-3-[3-(4-acetyl-3-hydroxy-2-propylphenoxy)-propoxy]-2-propylphenoxy]acetic acid ethyl ester A mixture of 1.17 g of 1-(2,4-dihydroxy-3-propylphenyl)ethanone, 2.41 g of 4-acetyl-3-(3-bromopropoxy)-2-propylphenoxy acetic acid ethyl ester, 1.66 g of anhydrous potassium carbonate and 0.1 g of potassium iodide in 15 ml of anhydrous acetone and 15 ml of anhydrous dimethylformamide was stirred at reflux for 18 hours. The solvent was removed in vacuo, 50 ml of 0.1N hydrochloric acid was added to the residue and the product was extracted with methylene chloride. The dried, over sodium sulfate, extract was concentrated in vacuo and the crude product was crystallized from methanol to yield 2.1 g, mp 45°–46°, (68% yield) of [4-acetyl-3-[3-(4-acetyl-3-hydroxy-2-propylphenoxy)propoxy]-2-propylphenoxy]acetic acid ethyl ester.

EXAMPLE 4 preparation of [4-acetyl-3-[3-(4-acetyl-3-hydroxy-2-propylphenoxy)-propoxy]-2-propylphenoxyacetic acid A suspension of 1.94 g of [4-acetyl-3-[3-(4-acetyl-3-hydroxy-2-propylphenoxy)propoxy]-2-propylphenoxy]acetic acid ethyl ester in 5 ml of ethanol and 20 ml of 1.0N sodium hydroxide was refluxed for 1 hour. After cooling, ice water was added and the mixture was acidified. The precipitate was extracted with methylene chloride. The dried, over magnesium sulfate, extract was concentrated in vacuo to an oil. Crystallization from ether-hexane gave 1.29 g, mp 124°–125°, (71% yield) of [4-acetyl-3-[3-(4-acetyl-3-hydroxy-2-propylphenoxy)propoxy]-2-propylphenoxy]acetic acid.

EXAMPLE 5

Preparation of [4-acetyl-3-(oxiranylmethoxy)-2-propylphenoxy]acetic acid methyl ester A mixture of 7.75 g of (4-acetyl-3-hydroxy-2-propylphenoxy)acetic acid methyl ester, 7.5 ml of epibromohydrin, 4.8 g of potassium iodide and 6.0 g of anhydrous potassium carbonate in 80 ml of anhydrous acetone and 40 ml of anhydrous dimethylformamide was stirred at reflux for 50 hours. The reaction mixture was filtered and the filtrate was concentrated in vacuo to an oil which was purified by high pressure liquid chromatography (HPLC) using 10% ethyl acetate-hexane to yield 6.16 g of [4-acetyl-3-(oxiranylmethoxy)-2-propylphenoxy]acetic acid methyl ester.

EXAMPLE 6

Preparation of racemic [4-acetyl-3-[3-(4-acetyl-3-hydroxy-2-propylphenoxy)-2-hydroxypropoxy]-2-propylphenoxy]acetic acid methyl ester A solution of 5.00 g of [4-acetyl-3-(oxiranylmethoxy)-2-propylphenoxy]acetic acid methyl ester, 2.70 g of 1-(2,4-dihydroxy-3-propylphenyl)ethanone and 2 drops of Triton B in 30 ml of anhydrous dimethylformamide was stirred at reflux for 6 hours. The solvent was removed in vacuo to give an oil which was purified by high pressure liquid chromatography using 50% ethyl acetate-hexane to yield 2.38 g, mp 124°–126°, of racemic [4-acetyl-3-[3-(4-acetyl-3-hydroxy-2-propylphenoxy)-2-hydroxypropoxy]-2-propylphenoxy]acetic acid methyl ester.

EXAMPLE 7

Preparation of racemic [4-acetyl-3-[3-(4-acetyl-3-hydroxy-2-propylphenoxy)-2-hydroxypropoxy]-2-propylphenoxy]acetic acid 0.25 molar hydrate A solution of 2.28 g of racemic [4-acetyl-3-[3-(4-acetyl-3-hydroxy-2-propylphenoxy)-2-hydroxypropoxy]-2-propylphenoxy]acetic acid in 50 ml of methanol and 22 ml of 1.0N sodium hydroxide was stirred at reflux for 90 minutes. The methanol was removed in vacuo and 6N hydrochloric acid was added to the residue to adjust the pH to 2.0. The resultant solid was filtered and recrystallized from ethyl acetate-hexane to give 1.90 g, mp 131°–134°, of racemic [4-acetyl-3-[3-(4-acetyl-3- hydroxy-2-propylphenoxy)-2-hydroxypropoxy]-2-propylphenoxy]acetic acid 0.25 molar hydrate.

EXAMPLE 8

Preparation of [4-acetyl-3-[(5-bromopentyl)oxy]-2-propylphenoxy]acetic acid ethyl ester A mixture of 6.0 g of (4-acetyl-3-hydroxy-2-propylphenoxy)acetic acid ethyl ester, 29 ml of 1,5-dibromopentane and 2.2 g of anhydrous potassium carbonate in 150 ml of anhydrous acetone was stirred at reflux. Additional portions (2.2 g) of potassium carbonate were added at 5, 21, 29 and 38 hours. Reflux was maintained for a total of 69 hours. The reaction mixture was filtered and the filtrate was concentrated in vacuo to a yellow oil which was purified by chromatography on 100 g of silica gel. Elution with 25% ethyl acetate-hexane gave 9.2 g (100%) of [4-acetyl-3-[(5-bromopentyl)oxy]-2-propylphenoxy]acetic acid ethyl ester as an oil.

EXAMPLE 9

Preparation of [4-acetyl-3-[5-(4-acetyl-3-hydroxy-2-propylphenoxy)-pentyloxy]-2-propylphenoxy]acetic acid ethyl ester A mixture of 3.0 g of 1-[2,4-dihydroxy-3-propylphenyl)ethanone, 6.65 g of [4-acetyl-3-[(5-bromopentyl)oxy]-2-propylphenoxy]acetic acid ethyl ester and 4.3 g of anhydrous potassium carbonate in 100 ml of anhydrous acetone and 50 ml of anhydrous dimethylformamide was stirred at reflux for 24 hours. The reaction mixture was concentrated in vacuo to a red oil which was purified by high pressure liquid chromatography using 25% ethyl acetate-hexane to yield 4.95 g (59%) of [4-acetyl-3-[5-(4-acetyl-3-hydroxy-2-propylphenoxy)pentyloxy]-2-propylphenoxy] acetic acid ethyl ester as a yellow oil.

EXAMPLE 10

Preparation of [4-acetyl-3-[5-(4-acetyl-3-hydroxy-2-propylphenoxy)-pentyloxy]-2-propylphenoxy]acetic acid A solution of 4.8 g of [4-acetyl-3-[5-(4-acetyl-3-hydroxy-2-propylphenoxy)pentyloxy]-2-propylphenoxy]acetic acid ethyl ester in 100 ml of methanol and 44 ml of 1N sodium hydroxide was stirred at reflux for 2 hours. The methanol was removed in vacuo and the pH of the residue was adjusted to 2.0. The product was filtered and recrystallized from ether-hexane to give 4.00 g (88%), mp 86°-89°, of [4-acetyl-3-[5-(4-acetyl-3-hydroxy-2-propylphenoxy)pentyloxy]-2-propylphenoxy]acetic acid.

EXAMPLE 11

Preparation of (4-acetyl-3-hydroxyphenoxy)acetic acid methyl ester

A mixture of 10.0 g of 1-(2,4-dihydroxyphenyl)ethanone, 6.2 ml of methyl bromoacetate, and 13.6 g of anhydrous potassium carbonate in 125 ml of anhydrous acetone was stirred at reflux for 3 hours. The reaction mixture was filtered and the filtrate was concentrated in vacuo to a solid which was recrystallized from methylene chloride-ether to give 9.45 g (64%), mp 101°-103°, of (4-acetyl-3-hydroxyphenoxy)acetic acid methyl ester.

EXAMPLE 12

Preparation of [4-acetyl-3-(3-bromopropoxy)phenoxy]acetic acid methyl ester

A mixture of 9.3 g of (4-acetyl-3-hydroxyphenoxy)acetic acid methyl ester, 21 ml of 1,3-dibromopropane and 8.6 g of anhydrous potassium carbonate in 500 ml of anhydrous acetone was stirred at reflux for 23 hours. An additional 21 ml of 1,3-dibromopropane and 8.6 g of potassium carbonate were added and reflux was continued for 22 hours. The reaction mixture was filtered and the filtrate was concentrated in vacuo to an oil which was purified by high pressure liquid chromatography using 10% ethyl acetate-toluene to yield 12.5 g (87%), mp 67°-70°, of [4-acetyl-3-(3-bromopropoxy)phenoxy]acetic acid methyl ester.

EXAMPLE 13

Preparation of [4-acetyl-3-[3-(4-acetyl-3-hydroxy-2-propylphenoxy)-propoxy]phenoxy]acetic acid methyl ester A mixture of 3.88 g of 1-(2,4-dihydroxy-3-propylphenyl)ethanone, 6.90 g of [4-acetyl-3-(3-bromopropoxy)phenoxy]acetic acid methyl ester, 5.5 g of anhydrous potassium carbonate in 100 ml of anhydrous acetone and 50 ml of anhydrous dimethylformamide was stirred at reflux for 20 hours. The solvent was removed in vacuo to a dark solid which was chromatographed on 100 g of silica gel. Elution with 30% ethyl acetate-toluene followed by recrystallization from methylene chloride-ether gave 4.85 g (53%), mp 103°-106°, of [4-acetyl-3-[3-(4-acetyl-3-hydroxy-2-propylphenoxy)-propoxy]phenoxy]acetic acid methyl ester.

EXAMPLE 14

Preparation of [4-acetyl-3-[3-(4-acetyl-3-hydroxy-2-propylphenoxy)-propoxy]phenoxy]acetic acid A solution of 4.74 g of [4-acetyl-3-[3-(4-acetyl-3-hydroxy-2-propylphenoxy)propoxy]phenoxy]acetic acid methyl ester in 150 ml of methanol and 52 ml of 1N sodium hydroxide was stirred at reflux for 75 minutes. The methanol was removed in vacuo and the pH of the residue was adjusted to 2.0 with 6N hydrochloric acid. The solid was filtered and dried to give 4.39 g (95%), mp 151°-155°, of [4-acetyl-3-[3-(4-acetyl-3-hydroxy-2-propylphenoxy)propoxy]phenoxy]acetic acid.

EXAMPLE 15

Preparation of [6-acetyl-3-(3-bromopropoxy)-2-propylphenoxy]acetic acid methyl ester A mixture of 5.0 g of 1-[4-(3-bromopropoxy)-2-hydroxy-3-propylphenyl]ethanone, 3.0 ml of methyl bromoacetate, and 3.3 g of anhydrous potassium carbonate in 75 ml of anhydrous acetone was stirred at reflux for 4 hours. An additional 2.0 g of potassium carbonate was added and reflux was continued for 13 hours. The reaction mixture was filtered and the filtrate was concentrated in vacuo to an oil which was purified by high pressure liquid chromatography using 5% ethyl acetate-toluene to give 3.5 g (58%) of [6-acetyl-3-(3-bromopropoxy)-2-propylphenoxy]acetic acid methyl ester as an oil.

EXAMPLE 16

Preparation of
[6-acetyl-[3-[3-(4-acetyl-3-hydroxy-2-propylphenoxy)-propoxy]-2-propylphenoxy]acetic acid methyl ester A mixture of 1.72 g of 1-(2,4-dihydroxy-3-propylphenyl)ethanone, 3.43 g of [6-acetyl-3-(3-bromopropoxy)-2-propylphenoxy]acetic acid methyl ester, 2.44 g of anhydrous potassium carbonate in 50 ml of anhydrous acetone and 25 ml of anhydrous dimethylformamide was stirred at reflux for 18 hours. The reaction mixture was concentrated in vacuo and the residue was purified by high pressure liquid chromatography to give 1.45 g (33%) of [6-acetyl-3-[3-(4-acetyl-3-hydroxy-2-propylphenoxy)propoxy]-2-propylphenoxy]acetic acid methyl ester as an oil.

EXAMPLE 17

Preparation of
[6-acetyl-3-[3-(4-acetyl-3-hydroxy-2-propylphenoxy)-propoxy]-2-propylphenoxy]acetic acid A solution of 1.41 g of [6-acetyl-3-[3-(4-acetyl-3-hydroxy-2-propylphenoxy)propoxy]-2-propylphenoxy]acetic acid methyl ester in 50 ml of methanol and 14 ml of 1N sodium hydroxide was stirred at reflux for 22 hours. The methanol was removed in vacuo and the pH of the residue was adjusted to 2.0 with 6N hydrochloric acid. The gummy product was extracted with ether and the crude extract was purified by chromatography on 60 g of silica gel. Elution with a solvent mixture of toluene:ethyl acetate:acetic acid (65:25:10) gave, after recrystallization from methylene chlorideether, 0.51 g (38%), mp 151°–155°, of [6-acetyl-3-[3-(4-acetyl-3-hydroxy-2-propylphenoxy)propoxy]-2-propylphenoxy]acetic acid.

EXAMPLE 18

Preparation of
4-(4-acetyl-3-hydroxy-2-propylphenoxy)butanoic acid ethyl ester

A mixture of 15.0 g of 1-(2,4-dihydroxy-3-propylphenyl)ethanone, 15.0 g of ethyl 4-bromobutyrate, 16.0 g of anhydrous potassium carbonate in 200 ml of anhydrous dimethylformamide was stirred and heated at 75° for 24 hours. The solvent was removed in vacuo and the residue was purified by high pressure liquid chromatography using 2.5% ethyl acetate-toluene to yield 7.62 g of 4-(4-acetyl-3-hydroxy-2-propylphenoxy)butanoic acid ethyl ester as an oil.

EXAMPLE 19

Preparation of
4-[4-acetyl-3-(3-bromopropoxy)-2-propylphenoxy]-butanoic acid ethyl ester A mixture of 7.6 g of 4-(4-acetyl-3-hydroxy-2-propylphenoxy)butanoic acid ethyl ester, 25 ml 1,3-dibromopropane and 2.0 g of anhydrous potassium carbonate in 200 ml of anhydrous acetone was stirred at reflux. Additional 2.0 g portions of potassium carbonate were added at 3, 7, 21, 47 and 55 hours. After a total reflux time of 78 hours, the reaction mixture was filtered and the filtrate was concentrated in vacuo to yield 4-[4-acetyl-3-(3-bromopropoxy)-2-propylphenoxy]butanoic acid ethyl ester as a slightly impure oil.

EXAMPLE 20

Preparation of
4-4-acetyl-3-[3-(4-acetyl-3-hydroxy-2-propylphenoxy)-propoxy]-2-propylphenoxy]butanoic acid ethyl ester A mixture of 3.00 g of 1-(2,4-dihydroxy-3-propylphenyl)ethanone, 6.65 g of 4-[4-acetyl-3-(3-bromopropoxy)-2-propylphenoxy]butanoic acid ethyl ester and 4.30 g of anhydrous potassium carbonate in 100 ml of anhydrous acetone and 50 ml of anhydrous dimethylformamide was stirred at reflux for 19 hours. The solvent was removed in vacuo to give a red oil which was purified by high pressure liquid chromatography to yield 6.42 g (76%) of 4-[4-acetyl-3-[3-(4-acetyl-3-hydroxy-2-propylphenoxy)propoxy]-2-propylphenoxy]butanoic acid ethyl ester as an oil.

EXAMPLE 21

Preparation of
4-[4-acetyl-3-[3-(4-acetyl-3-hydroxy-2-propylphenoxy)-propoxy]-2-propylphenoxy]butanoic acid A solution of 6.22 g of 4-[4-acetyl-3-[3-(4-acetyl-3-hydroxy-2-propylphenoxy)propoxy]-2-propylphenoxy]butanoic acid ethyl ester in 100 ml of methanol and 57 ml of 1N sodium hydroxide was stirred at reflux for 2 hours. The solvent was removed in vacuo and the pH of the residue was adjusted to 2.0 with 6N hydrochloric acid. The solid was filtered and dried to give 5.16 g (87%), mp 96°–99°, 4-[4-acetyl-3-[3-(4-acetyl-3-hydroxy-2-propylphenoxy)propoxy]-2-propylphenoxy]butanoic acid.

EXAMPLE 22

Preparation of
racemic-(4-acetyl-3-hydroxy-2-propylphenoxy)-alpha-methylacetic acid ethyl ester A mixture of 10.0 g of 1-(2,4-dihydroxy-3-propylphenyl)ethanone, 8.4 ml of ethyl 2-bromopropionate and 10.7 g of anhydrous potassium carbonate in 125 ml of anhydrous acetone was stirred at reflux for 42 hours. The reaction mixture was filtered and the filtrate was concentrated to an oil which was purified by high pressure liquid chromatography using 2% ethyl acetate-toluene to yield 11.4 g (73%) of racemic-(4-acetyl-3-hydroxy-2-propylphenoxy)-alpha-methylacetic acid ethyl ester as an oil.

EXAMPLE 23

Preparation of
racemic-[4-acetyl-3-(3-bromopropoxy)-2-propylphenoxy]methylacetic acid ethyl ester A mixture of 6.4 g of racemic-(4-acetyl-3-hydroxy-2-propylphenoxy)-alphamethylacetic acid ethyl ester, 22 ml of 1,3-dibromopropane and 4.5 g of anhydrous potassium carbonate in 175 ml of anhydrous acetone was stirred at reflux for 52 hours. The reaction mixture was filtered and the filtrate was concentrated in vacuo to 9.0 g of racemic-[4-acetyl-3-(3-bromopropoxy)-2-propylphenoxy]methylacetic acid as a yellow oil.

EXAMPLE 24

Preparation of racemic
[4-acetyl-3-[3-(4-acetyl-3-hydroxy-2-propylphenoxy)-propoxy]-2-propylphenoxy]methylacetic acid ethyl ester A mixture of 3.0 g of 1-(2,4-dihydroxy-3-propylphenyl)ethanone, 6.4 g of racemic-[4-acetyl-3-(3-bromopropoxy)-2-propylphenoxy]methylacetic acid ethyl ester and 4.3 g of anhydrous potassium carbonate in 100 ml of anhydrous acetone and 50 ml of anhydrous dimethylformamide was stirred at reflux for 20 hours. The reaction mixture was filtered and the filtrate was concentrated in vacuo to a red oil which was purified by high pressure liquid chromatography using 25% ethyl acetate-hexane to give 5.6 g (69%) of racemic-[4-acetyl-3-[3-(4-acetyl-3-hydroxy-2-propylphenoxy)-propoxy]-2-propylphenoxy]methylacetic acid ethyl ester as a yellow oil.

EXAMPLE 25

Preparation of
racemic-[4-acetyl-3-[3-(4-acetyl-3-hydroxy-2-propylphenoxy)propoxy]-2-propylphenoxy]methylacetic acid A mixture of 5.4 g of racemic-[4-acetyl-3-[3-(4-acetyl-3-hydroxy-2-propylphenoxy)propoxy]-2-propylphenoxy]methylacetic acid ethyl ester in 100 ml of methanol and 50 ml of 1N sodium hydroxide was stirred at reflux for 2 hours. The methanol was removed in vacuo and the pH of the residue was adjusted to 2.0 with 6N hydrochloric acid. The gummy product was extracted with methylene chloride and the extract was dried over magnesium sulfate and concentrated in vacuo to an oil. The crude acid was dissolved in 50 ml of methanol and 10 ml of 1.0N sodium hydroxide was added. The methanol was removed in vacuo, 25 ml of water was added and the sodium salt (0.33 molar hydrate) of racemic-[4-acetyl-3-[3-(4-acetyl-3-hydroxy-2-propylphenoxy)propoxy]-2-propylphenoxy]methylacetic acid was filtered and dried to give 4.2 g (78%), mp 92°–95°. The sodium salt was converted with 1N hydrochloric acid to the acid, which crystallized on addition of hexane. Filtration gave racemic-[4-acetyl-3-[3-(4-acetyl-3-hydroxy-2-propylphenoxy)propoxy]-2-propylphenoxy]methylacetic acid, mp 123°–126°.

EXAMPLE 26

Preparation of
[4-acetyl-3-[2-(2-chloroethoxy)ethoxy]-2-propylphenoxy]acetic acid ethyl ester A mixture of 6.0 g of (4-acetyl-3-hydroxy-2-propylphenoxy)acetic acid ethyl ester, 25 ml of bis(2-chloroethyl)ether and 2.2 g of anhydrous potassium carbonate in 150 ml of anhydrous acetone was stirred at reflux. After 24 hours, 2 g of potassium iodide and 50 ml of anhydrous dimethylformamide were added and reflux was continued. After 50 hours, 2.2 g of potassium carbonate and 2 g of potassium iodide were added and after 77 hours, 2.0 g of potassium carbonate was added. After a total reflux time of 108 hours, the reaction mixture was concentrated in vacuo and the residue was purified by high pressure liquid chromatography using 25% ethyl acetate-hexane to give 5.96 g (72% yield) of [4-acetyl-3-[2-(2-chloroethoxy)ethoxy]-2-propylphenoxy]acetic acid ethyl ester as an oil.

EXAMPLE 27

Preparation of
[4-acetyl-3-[2-[2-(4-acetyl-3-hydroxy-2-propylphenoxy)ethoxy]ethoxy]-2-propylphenoxy]acetic acid ethyl ester A mixture of 2.94 g of 1-(2,4-dihydroxy-3-propylphenyl)ethanone, 5.85 g of [4-acetyl-3-[2-(2-chloroethoxy)ethoxy]-2-propylphenoxy]acetic acid ethyl ester, 4.2 g of anhydrous potassium carbonate, and 2.25 g of potassium iodide in 100 ml of anhydrous acetone and 50 ml of anhydrous dimethylformamide was stirred at reflux. Additional 2.0 g portions of potassium carbonate were added after 19, 26 and 51 hours. Reflux was continued for a total of 8 days and then the reaction mixture was concentrated in vacuo. The crude product was purified by liquid chromatography using 35% ethyl acetate-hexane to give 5.8 g (70% yield) of [4-acetyl-3-[2-[2-(4-acetyl-3-hydroxy-2-propylphenoxy)ethoxy]ethoxy]-2-propylphenoxy]acetic acid ethyl ester.

EXAMPLE 28

Preparation of
[4-acetyl-3-[2-[2-(4-acetyl-3-hydroxy-2-propylphenoxy)ethoxy]ethoxy]-2-propylphenoxy]acetic acid A solution of 5.65 g of [4-acetyl-3-[2-[2-(4-acetyl-3-hydroxy-2-propylphenoxy)ethoxy]ethoxy]-2-propylphenoxy]acetic acid ethyl ester in 100 ml of methanol and 50 ml of 1N sodium hydroxide was stirred at reflux for 2 hours. The reaction mixture was concentrated in vacuo to remove the methanol and the pH of the residue was adjusted to 2.0 with 6N hydrochloric acid. The product was filtered and recrystallized from ether-hexane to give 4.3 g (80% yield), mp 96°–99°, of [4-acetyl-3-[2-[2-(4-acetyl-3-hydroxy-2-propylphenoxy)ethoxy]ethoxy]-2-propylphenoxy]acetic acid.

EXAMPLE 29

Preparation of
6-(4-acetyl-3-hydroxy-2-propylphenoxy)hexanoic acid methyl ester

A mixture of 5.0 g of 1-(2,4-dihydroxy-3-propylphenyl)ethanone, 5.4 g of methyl 6-bromohexanoate and 5.4 g of anhydrous potassium carbonate in 50 ml of anhydrous dimethylformamide was stirred and heated at 75° for 10 hours. The solvent was removed in vacuo and the residue was purified by column chromatography on 125 g of silica gel. Elution with 25% ethyl acetate-hexane gave 7.5 g (90% yield) of 6-(4-acetyl-3-hydroxy-2-propylphenoxy)hexanoic acid methyl ester as an oil.

EXAMPLE 30

Preparation of
6-[4-acetyl-3-(3-bromopropoxy)-2-propylphenoxy]hexanoic acid methyl ester A mixture of 6.0 g of 6-(4-acetyl-3-hydroxy-2-propylphenoxy)hexanoic acid methyl ester, 19 ml of 1,3-dibromopropane and 2.0 g of anhydrous potassium carbonate in 175 ml of anhydrous acetone was stirred at reflux for 52 hours. The reaction mixture was concentrated in vacuo to give 8.1 g (98% yield) of 6-[4-acetyl-3-(3-bromopropoxy)-2-propylphenoxy]hexanoic acid methyl ester as an oil.

EXAMPLE 31

Preparation of
6-[4-acetyl-3-[3-(4-acetyl-3-hydroxy-2-propylphenoxy)-propoxy]-2-propylphenoxy]hexanoic acid methyl ester A mixture of 2.62 g of 1-(2,4-dihydroxy-3-propylphenyl)ethanone, 6.00 g of 6-[4-acetyl-3-(3-bromopropoxy)-2-propylphenoxy]hexanoic acid methyl ester and 3.70 g of anhydrous potassium carbonate in 100 ml of anhydrous acetone and 50 ml of anhydrous dimethylformamide was stirred at reflux for 20 hours. The reaction mixture was concentrated in vacuo and the residue was purified by liquid chromatography using 30% ethyl acetate-hexane to give 5.10 g (68% yield) of 6-[4-acetyl-3-[3-(4-acetyl-3-hydroxy-2-propylphenoxy)propoxy]-2-propylphenoxy]hexanoic acid methyl ester as an oil.

EXAMPLE 32

Preparation of
6-[4-acetyl-3-[3-(4-acetyl-3-hydroxy-2-propylphenoxy)-propoxy]-2-propylphenoxy]hexanoic acid A solution of 4.95 g of 6-[4-acetyl-3-[3-(4-acetyl-3-hydroxy-2-propylphenoxy)propoxy]-2-propylphenoxy]hexanoic acid methyl ester and 45 ml of 1N sodium hydroxide in 100 ml of methanol was stirred at reflux for 2 hours. Most of the methanol was removed in vacuo and the pH of the residue was adjusted to 2.0. The resultant product was filtered and recrystallized from methylene chloride-hexane to yield 4.30 g (89% yield), mp 105°–108°, of 6-[4-acetyl-3-[3-(4-acetyl-3-hydroxy-2-propylphenoxy)propoxy]-2-propylphenoxy]hexanoic acid.

EXAMPLE 33

Preparation of
1-(5-bromo-2,4-dihydroxy-3-propylphenyl)ethanone

To a cold suspension (7°) of 5 g (0.026 mol) of 1-(2,4-dihydroxy-3-propylphenyl)ethanone in 150 ml of chloroform was added 27 ml (0.027 mol) of 1M bromine in chloroform dropwise. The mixture was stirred at 5° for 45 minutes and solvent was removed in vacuo. The residue was extracted with hot hexane and the hexane extract was boiled down to 50 ml and allowed to crystallize. Filtration gave 5.2 g, melting point 67° (74% yield) of 1-(5-bromo-2,4-dihydroxy-3-propylphenyl)ethanone.

EXAMPLE 34

Preparation of
[4-acetyl-3-[3-(4-acetyl-6-bromo-3-hydroxy-2-propylphenoxy)propoxy]-2-propylphenoxy]acetic acid methyl ester A mixture of 2 g (0.0073 mol) of 1-(5-bromo-2,4-dihydroxy-3-propylphenyl)-ethanone, 2.84 g (0.0073 mol) of [4-acetyl-3-(3-bromopropoxy)-2-propylphenoxy]acetic acid methyl ester and 1.52 g (0.011 mol) of anhydrous potassium carbonate in 150 ml of anhydrous acetone was stirred at reflux for 20 hours. An additional 1 g of potassium carbonate was added and reflux was continued for a total of 35 hours. The hot reaction mixture was filtered and the filtrate was concentrated in vacuo to a oil which was dissolved in ethyl acetate and washed with 1N sodium hydroxide and sodium chloride solution. The crude product was purified by HPLC, eluting with 25% ethyl acetate in hexane to yield 2.33 g (55% yield) of [4-acetyl-3-[3-(4-acetyl-6-bromo-3-hydroxy-2-propylphenoxy)propoxy]-2-propylphenoxy]acetic acid methyl ester as a pale yellow oil.

EXAMPLE 35

Preparation of
[4-acetyl-3-[3-(4-acetyl-6-bromo-3-hydroxy-2-propylphenoxy)propoxy]-2-propylphenoxy]acetic acid To a solution of 2.1 g (0.0037 mol) of [4-acetyl-3-[3-(4-acetyl-6-bromo-3-hydroxy-2-propylphenoxy)propoxy]-2-propylphenoxy]acetic acid methyl ester in 50 ml of methanol was added 50 ml (0.05 mol) of 1N sodium hydroxide. The mixture was stirred at 25° for 16 hours and acidified to pH 4. The gummy precipitate was dissolved in ethyl acetate and washed with sodium choloride solution. The gummy solid obtained on concentration of the ethyl acetate was purified by $C_{18}$ reverse phase column chromatography, eluting with 60% to 75% of methanol in water to yield 1.0 g, melting point 129°–130° (48% yield) of [4-acetyl-3-[3-(4-acetyl-6-bromo-3-hydroxy-2-propylphenoxy)propoxy]-2-propylphenoxy]acetic acid.

EXAMPLE 36

Preparation of
1-(5-chloro-2,4-dihydroxy-3-propylphenyl)ethanone

To a solution of 5.0 g (0.026 mol) of 1-(2,4-dihydroxy-3-propylphenyl)ethanone in 125 ml of chloroform was added 32.3 ml of (0.030 mol) 0.94M chlorine in chloroform dropwise at 25°. The mixture was stirred at 25° for 2.5 hours. The solvent was removed in vacuo and the residue was extracted with hot hexane. The hexane extract was boiled down to 100 ml and allowed to crystallize. Filtration gave 3.0 g, melting point 96°. (51% yield) of 1-(5-chloro-2,4-dihydroxy-3-propylphenyl)ethanone.

EXAMPLE 37

Preparation of
[4-acetyl-3-[3-(4-acetyl-6-chloro-3-hydroxy-2-propylphenoxy)propoxy]-2-propylphenoxy]acetic acid methyl ester A mixture of 2 g (0.0088 mol) of 1-(5-chloro-2,4-dihydroxy-3-propylphenyl)ethanone, 3.39 g (0.0088 mol) of [4-acetyl-3-(3-bromopropoxy)-2-propylphenoxy]acetic acid methyl ester and 1.8 g (0.013 mol) of anhydrous potassium carbonate in 150 ml of anhydrous acetone was stirred at reflux for 20 hours. An additional 1.0 g of potassium carbonate was added and reflux was continued for a total of 35 hours. The hot reaction mixture was filtered and filtrate was concentrated in vacuo to an oil which was dissolved in ethyl acetate and washed with 1N sodium hydroxide and sodium chloride solution. The crude oil obtained on concentration of the ethyl acetate solution was purified by HPLC, eluting with 30% ethyl acetate in hexane to yield 2.7 g (58% yield) of [4-acetyl-3-[3-(4-acetyl-6-chloro-3-hydroxy-2-propylphenoxy)propoxy]-2-propylphenoxy]acetic acid methyl ester as a pale yellow oil.

EXAMPLE 38

Preparation of
[4-acetyl-3-[3-(4-acetyl-6-chloro-3-hydroxy-2-propylphenoxy)propoxy]-2-propylphenoxy]acetic acid To a solution of 1.94 g (0.0036 mol) of [4-acetyl-3-[3-(4-acetyl-6-chloro-3-hydroxy-2-propylphenoxy)propoxy]-2-propylphenoxy]acetic acid methyl ester in 60 ml of methanol was added 60 ml of 1N sodium hydroxide (0.06 mol). The mixture was stirred at 25° for 20 hours. Most of the methanol was removed in vacuo and the aqueous solution was acidified to pH 4. The gummy precipitate was dissolved in ethyl acetate and washed with sodium chloride solution. The oil obtained on concentration of the ethyl acetate extract was purified by $C_{18}$ reverse phase column chromatography, eluting with 60-80% methanol in water to yield a pale yellow oil which solidified. Recrystallization from cyclohexane-ether gave 790 mg, melting point 119°-121° (42% yield) of [4-acetyl-3-[3-(4-acetyl-6-chloro-3-hydroxy-2-propylphenoxy)propoxy]-2-propylphenoxy]acetic acid.

EXAMPLE 39

Preparation of
4-[4-acetyl-3-[2-[2-[(methylsulfonyl)oxy]ethoxy]ethoxy]-2-propylphenoxy]butanoic acid ethyl ester A mixture of 4 g (0.013 mol) of 4-(4-acetyl-3-hydroxy-2-propylphenoxy)butanoic acid ethyl ester, 17 g (0.065 mol) of diethylene glycol dimesylate and 3.6 g (0.026 mol) of anhydrous potassium carbonate in 80 ml of anhydrous acetone and 40 ml of anhydrous dimethylformamide was stirred at reflux for 20 hours. An additional 1.8 g of potassium carbonate was added and reflux was continued for a total of 44 hours. The reaction mixture was filtered and concentrated in vacuo to an orange oil which was treated with ethyl acetate and sodium chloride solution. The yellow oil obtained on concentration of the ethyl acetate was purified by HPLC, eluting with 15% ethyl acetate/toluene to yield 4.1 g (67% yield) of 4-[4-acetyl-3-[2-[2-[(methylsulfonyl)oxy]ethoxy]-ethoxy]-2-propylphenoxy]butanoic acid ethyl ester as a yellow oil.

EXAMPLE 40

Preparation of
[4-acetyl-3-[2-[2-(4-acetyl-6-chloro-3-hydroxy-2-propylphenoxy)ethoxy]ethoxy]2-propylphenoxy]acetic acid ethyl ester A mixture of 0.512 g (0.00224 mol) of 1-(5-chloro-2,4-dihydroxy-3-propylphenyl)-ethanone, 1.000 g (0.00224 mol) of [4-acetyl-3-[2-[2-[(methylsulfonyl)oxy]ethoxy]-ethoxy]-2-propylphenoxy]acetic acid ethyl ester and 0.620 g (0.00448 mol) of anhydrous potassium carbonate in 20 ml of anhydrous acetone and 10 ml of anhydrous dimethylformamide was stirred at reflux for 24 hours. The reaction mixture was filtered and concentrated in vacuo to an oil which was treated with ethyl acetate and sodium chloride solution. The crude oil obtained on concentration of the ethyl acetate was purified by column chromatography, eluting with 20-30% ethyl acetate-hexane to yield 0.400 g (31% yield) of [4-acetyl-3-[2-[2-(4-acetyl-6-chloro-3-hydroxy-2-propylphenoxy)ethoxy]ethoxy]2-propylphenoxy]acetic acid ethyl ester as a pale yellow oil.

EXAMPLE 41

Preparation of
[4-acetyl-3-[2-[2-(4-acetyl-6-chloro-3-hydroxy-2-propylphenoxy)ethoxy]ethoxy]-2-propylphenoxy]acetic acid To a solution of 0.400 g (0.00069 mol) of [4-acetyl-3-[2-[2-(4-acetyl-6-chloro-3-hydroxy-2-propylphenoxy)ethoxy]ethoxy]-2-propylphenoxy]acetic acid ethyl ester in 15 ml of methanol was added 15 ml of 1N sodium hydroxide (0.015 mol). The mixture was stirred at 25° for 5 hours and the methanol was removed in vacuo. The aqueous solution was acidified to pH 4, the gummy precipitate was dissolved in ethyl acetate and washed with sodium chloride solution. The oil obtained on concentration of the ethyl acetate was crystallized from cyclohexane to give 0.32 g, melting point 89°-91° (84% yield) of [4-acetyl-3-[2-[2-(4-acetyl-6-chloro-3-hydroxy-2-propylphenoxy)ethoxy]ethoxy]-2-propylphenoxy]acetic acid.

EXAMPLE 42

Preparation of
4-[4-acetyl-3-[2-[2-(4-acetyl-3-hydroxy-2-propylphenoxy)ethoxy]ethoxy]-2-propylphenoxy]butanoic acid ethyl ester A mixture of 1 g (0.0052 mol) of 1-(2,4-dihydroxy-3-propylphenyl)ethanone, 2.45 g (0.0052 mol) of 4-[4-acetyl-3-[2-[2-[(methylsulfonyl)oxy]ethoxy]-ethoxy]-2-propylphenoxy]butanoic acid ethyl ester and 2.6 g (0.019 mol) of anhydrous potassium carbonate in 100 ml of anhydrous acetone and 50 ml of anhydrous dimethylformamide was stirred at reflux for 19 hours. The reaction mixture was filtered and the filtrate was concentrated in vacuo to an oil which was treated with ethyl acetate and sodium chloride solution. The organic phase was washed with 1N sodium hydroxide solution and sodium chloride solution. The yellow oil obtained on concentration of the ethyl acetate was purified by column chromatography, eluting with 5% ethyl acetate-toluene to yield 0.526 g (18% yield) of 4-[4-acetyl-3-[2-[2-(4-acetyl-3-hydroxy-2-propylphenoxy)ethoxy]ethoxy]-2-propylphenoxy]butanoic acid ethyl ester as a pale yellow oil.

EXAMPLE 43

Preparation of
4-[4-acetyl-3-[2-[2-(4-acetyl-3-hydroxy-2-propylphenoxy)ethoxy]ethoxy]-2-propylphenoxy]butanoic acid To a solution of 0.526 g (0.0009 mol) of 4-[4-acetyl-3-[2-[2-(4-acetyl-3-hydroxy-2-propylphenoxy)ethoxy]ethoxy]-2-propylphenoxy]butanoic acid ethyl ester in 23 ml of methanol was added 23 ml (0.023 mol) of 1N sodium hydroxide. The mixture was stirred at 25° for 6 hours and the methanol was removed in vacuo. The aqueous solution was acidified to pH 3, the precipitate was dissolved in ethyl acetate and washed with sodium chloride solution. The oil obtained on concentration of the ethyl acetate was purified by column chromatography, eluting with 50% ethyl acetate-hexane and ethyl acetate to yield 0.4 g (80% yield) of 4-[4-acetyl-3-[2-[2-(4-acetyl-3-hydroxy-2-propylphenoxy)ethoxy]ethoxy]-2-propylphenoxy]butanoic acid as a pale yellow oil which solidified (melting point 52°-58°).

EXAMPLE 44

Preparation of
[4-acetyl-3-[2-[2-[2-[(methylsulfonyl)oxy]ethoxy]ethoxy]ethoxy]-2-propylphenoxy]acetic acid ethyl ester A mixture of 3.3 g (0.012 mole) of (4-acetyl-3-hydroxy-2-propylphenoxy)acetic acid ethyl ester, 18.0 g (0.059) of triethyleneglycol dimesylate and 3.3 g (0.024 mole) of anhydrous potassium carbonate in 100 ml of anhydrous acetone and 45 ml of anhydrous dimethylformamide was stirred at reflux for 26 hours. The reaction mixture was concentrated in vacuo to yield an oil which was dissolved in 60% ethyl acetate-toluene and passed through a column of 60 g of silica gel. The eluent was concentrated in vacuo and purified by HPLC using 35% ethyl acetate-toluene to give 3.06 g (53% yield) of [4-acetyl-3-[2-[2-[2-[(methylsulfonyl)oxy]ethoxy]ethoxy]ethoxy]-2-propylphenoxy]acetic acid ethyl ester as an oil.

EXAMPLE 45

Preparation of [4-acetyl-3-[2-[2-[2-(4-acetyl-3-hydroxy-2-propylphenoxy)ethoxy]ethoxy]ethoxy]-2-propylphenoxy]acetic acid ethyl ester A mixture of 1.16 g (0.006 mole) of 1-(2,4-dihydroxy-3-propylphenyl)ethanone, 2.93 g (0.006 mole) of [4-acetyl-3-[2-[2-[2-[(methylsulfonyl)oxy]ethoxy]ethoxy]ethoxy]-2-propylphenoxy]acetic acid ethyl ester and 1.65 g (0.012 mole) of anhydrous potassium carbonate in 50 ml of anhydrous acetone and 25 ml of anhydrous dimethylformamide was stirred at reflux for 21 hours. The solvents were removed in vacuo and the residue was purified by HPLC using 40% ethyl acetate-hexane to give 2.45 g (70% yield) of [4-acetyl-3-[2-[2-[2-(4-acetyl-3-hydroxy-2-propylphenoxy)ethoxy]ethoxy]ethoxy]-2-propylphenoxy]acetic acid ethyl ester as an oil.

EXAMPLE 46

Preparation of [4-acetyl-3-[2-[2-[2-(4-acetyl-3-hydroxy-2-propylphenoxy)ethoxy]ethoxy]ethoxy]-2-propylphenoxy]acetic acid A solution of 2.35 g (0.004 mole) of [4-acetyl-3-[2-[2-[2-(4-acetyl-3-hydroxy-2-propylphenoxy)ethoxy]ethoxy]ethoxy]-2-propylphenoxy]acetic acid ethyl ester in 50 ml of methanol and 20 ml (0.02 mole) of 1.0N sodium hydroxide was stirred at reflux for 90 minutes. Most of the solvent was removed in vacuo and the pH of the residue was adjusted to 2.0 with 6N HCl. The gummy product was extracted with methylene chloride. The dried (magnesium sulfate) extract was concentrated in vacuo and the residue was crystallized from methylene chloride-hexane to give 2.06 g (92% yield) of [4-acetyl-3-[2-[2-[2-(4-acetyl-3-hydroxy-2-propylphenoxy)ethoxy]ethoxy]ethoxy]-2-propylphenoxy]acetic acid, mp 74°–77°.

EXAMPLE 47

Preparation of 6-[4-acetyl-3-[2-[2-[(methylsulfonyl)oxy]ethoxy]ethoxy]-2-propylphenoxy]hexanoic acid methyl ester A mixture of 4.0 g (0.012 mole) of 6-(4-acetyl-3-hydroxy-2-propylphenoxy)hexanoic acid methyl ester, 16.3 g (0.062 mole) of diethyleneglycol dimesylate and 3.4 g (0.024 mole) of anhydrous potassium carbonate in 90 ml of anhydrous acetone and 4 ml of anhydrous dimethylformamide was stirred at reflux for 22 hours. The solvents were removed in vacuo and the residue was treated with 100 ml of 50% ethyl acetate-hexane. Some of the residual starting dimesylate was insoluble and was removed by filtration. The filtrate was concentrated in vacuo and the residual oil was purified by HPLC to give 4.8 g (80% yield) of 6-[4-acetyl-3-[2-[2-[(methylsulfonyl)oxy]ethoxy]ethoxy]-2-propylphenoxy]hexanoic acid methyl ester as an oil.

EXAMPLE 48

Preparation of 6-[4-acetyl-3-[2-[2-(4-acetyl-3-hydroxy-2-propylphenoxy)ethoxy]ethoxy]-2-propylphenoxy]hexanoic acid methyl ester A mixture of 1.14 g (0.0059 mole) of 1-(2,4-dihydroxy-3-propylphenyl)ethanone, 2.87 g (0.0059 mole) of 6-[4-acetyl-3-[2-[2-[(methylsulfonyl)oxy]ethoxy]ethoxy]-2-propylphenoxy]hexanoic acid methyl ester and 1.62 g (0.012 mole) of anhydrous potassium carbonate in 50 ml of anhydrous acetone and 25 ml of anhydrous dimethylformamide was stirred at reflux for 17 hours. The solvents were removed in vacuo and the residue was purified by HPLC using 35% ethyl acetate-hexane to yield 2.65 g (77% yield) of 6-[4-acetyl-3-[2-[2-(4-acetyl-3-hydroxy-2-propylphenoxy)ethoxy]ethoxy]-2-propylphenoxy]hexanoic acid methyl ester.

EXAMPLE 49

Preparation of 6-[4-acetyl-3-[2-[2-(4-acetyl-3-hydroxy-2-propylphenoxy)ethoxy]ethoxy]-2-propylphenoxy]hexanoic acid A solution of 2.55 g (0.0044 mole) of 6-[4-acetyl-3-[2-[2-(4-acetyl-3-hydroxy-2-propylphenoxy)ethoxy]ethoxy]-2-propylphenoxy]hexanoic acid methyl ester in 50 ml of methanol and 22 ml (0.022 mole) of 1.0N sodium hydroxide was stirred at reflux for 90 minutes. Most of the solvent was removed in vacuo and the pH of the residue was adjusted to 2.0 with 6N hydrochloric acid. The gummy product was extracted with ethyl acetate and the dried (magnesium sulfate) extract was concentrated in vacuo to an oil which slowly crystallized. Trituration with hexane and filtration gave 2.14 g which was purified by chromatography on 50 g of silica gel. Elution with 60% ethyl acetate-hexane gave the pure product which was triturated with hexane and filtered to yield 1.52 g (61% yield), melting point 55°–57°, of 6-[4-acetyl-3-[2-[2-(4-acetyl-3-hydroxy-2-propylphenoxy)ethoxy]ethoxy]-2-propylphenoxy]hexanoic acid.

EXAMPLE 50

Preparation of [4-acetyl-3-[2-[2-[2-(2-bromoethoxy)ethoxy]ethoxy]-2-propylphenoxy]acetic acid ethyl ester A mixture of 2.8 g (0.01 mole) of (4-acetyl-3-hydroxy-2-propylphenoxy)acetic acid ethyl ester, 11.0 g (0.034 mole) of 1,11-dibromo-3,6,9-trioxaundecane and 2.8 g (0.02 mole) of anhydrous potassium carbonate in 60 ml of anhydrous acetone and 30 ml of anhydrous dimethylformamide was stirred at reflux for 16 hours. An additional 1.4 g of potassium carbonate was added and reflux was continued for 24 hours. The solvents were removed in vacuo and the residue was chromatographed on 200 g of silica gel. Elution with 10% ethyl acetate-toluene gave 3.2 g (62% yield) of [4-acetyl-3-[2-[2-[2-(2-bromoethoxy)ethoxy]ethoxy]ethoxy]-2-propylphenoxy]acetic acid ethyl ester as an oil.

EXAMPLE 51

Preparation of
[4-acetyl-3-[2-[2-[2-[2-(4-acetyl-3-hydroxy-2-propyl-phenoxy)ethoxy]ethoxy]ethoxy]ethoxy]-2-propyl-phenoxy]acetic acid ethyl ester A mixture of 2.55 g (0.005 mole) of [4-acetyl-3-[2-[2-[2-(2-bromoethoxy)ethoxy]ethoxy]ethoxy]-2-propyl-phenoxy]acetic acid ethyl ester, 0.97 g (0.005 mole) of 1-(2,4-dihydroxy-3-propylphenyl)ethanone and 1.00 g (0.0062 mole) of anhydrous potassium carbonate in 60 ml of anhydrous acetone was stirred at reflux for 15 hours. An additional 0.5 g of potassium carbonate was added and reflux was continued for 15 hours. The solvent was removed in vacuo and the residue was chromatographed on 300 g of silica gel. Elution with 30% ethyl acetate-toluene gave 1.25 g (40% yield) of [4-acetyl-3-[2-[2-[2-[2-(4-acetyl-3-hydroxy-2-propyl-phenoxy)ethoxy]ethoxy]ethoxy]ethoxy]-2-propyl-phenoxy]acetic acid ethyl ester as an oil.

EXAMPLE 52

Preparation of
[4-acetyl-3-[2-[2-[2-[2-(4-acetyl-3-hydroxy-2-propyl-phenoxy)ethoxy]ethoxy]ethoxy]ethoxy]-2-propyl-phenoxy]acetic acid A solution of 1.25 g (0.002 mole) of [4-acetyl-3-[2-[2-[2-[2-(4-acetyl-3-hydroxy-2-propylphenoxy)ethoxy]ethoxy]ethoxy]ethoxy]-2-propylphenoxy]acetic acid ethyl ester in 30 ml of methanol and 10 ml (0.01 mole) of 1.0N sodium hydroxide was stirred at reflux for 5 hours. Most of the solvent was removed in vacuo and the pH of the residue was adjusted to 2.0 with 6N hydrochloric acid. The product was extracted with methyl acetate and the dried (magnesium sulfate) extract was concentrated in vacuo to an oil which was purified by chromatography on 75 g of silica gel. Elution with toluene-ethyl acetate-acetic acid (65:25:10) gave 0.79 g (66% yield) of [4-acetyl-3-[2-[2-[2-[2-(4-acetyl-3-hydroxy-2-propylphenoxy)ethoxy]ethoxy]ethoxy]ethoxy]-2-propylphenoxy]acetic acid as an oil.

EXAMPLE 53

Preparation of
4-[4-acetyl-3-[(5-bromopentyl)oxy]-2-propylphenoxy]-butanoic acid ethyl ester A mixture of 3.5 g (0.011 mole) of 4-(4-acetyl-3-hydroxy-2-propylphenoxy)butanoic acid ethyl ester, 15.4 ml (0.11 mole) of 1,5-dibromopentane and 1.2 g (0.0087 mole) of anhydrous potassium carbonate in 60 ml of anhydrous acetone was stirred at reflux for 77 hours. During the reflux period additional 1.4 g portions of potassium carbonate were added at 4,21,28 and 45 hours. The solvent was removed in vacuo and the residue was purified by HPLC using 17% ethyl acetate-hexane to yield 4.35 g (84% yield) of 4-[4-acetyl-3-[(5-bromopentyl)oxy]-2-propylphenoxy]butanoic acid ethyl ester as an oil.

EXAMPLE 54

Preparation of
4-[4-acetyl-3-[[5-(4-acetyl-3-hydroxy-2-propylphenoxy)pentyl]oxy]-2-propylphenoxy]butanoic acid ethyl ester A mixture of 0.96 g (0.005 mole) of 1-(2,4-dihydroxy-3-propylphenyl)ethanone, 2.26 g (0.005 mole) of 4-[4-acetyl-3-[(5-bromopentyl)oxy]-2-propylphenoxy]-butanoic acid ethyl ester and 1.36 g (0.010 mole) of anhydrous potassium carbonate in 40 ml of anhydrous acetone and 20 ml of anhydrous dimethylformamide was stirred at reflux for 17 hours. The solvents were removed in vacuo and the residue was purified by HPLC using 25% ethyl acetate-hexane to yield 2.36 g (84% yield) of 4-[4-acetyl-3-[[5-(4-acetyl-3-hydroxy-2-propylphenoxy)pentyl]oxy]-2-propylphenoxy]butanoic acid ethyl ester as an oil.

EXAMPLE 55

Preparation of
4-[4-acetyl-3-[[5-(4-acetyl-3-hydroxy-2-propylphenoxy)pentyl]oxy]-2-propylphenoxy]butanoic acid A solution of 2.26 g (0.004 mole) of 4-[4-acetyl-3-[[5-(4-acetyl-3-hydroxy-2-propylphenoxy)pentyl]oxy]-2-propylphenoxy]butanoic acid ethyl ester in 50 ml of methanol and 20 ml (0.02 mole) of 1.0N sodium hydroxide was stirred at reflux for 3 hours. Most of the solvent was removed in vacuo and the pH of the residue was adjusted to 2.0 with 6N hydrochloric acid. The product was extracted with methylene chloride and the dried (magnesium sulfate) extract was concentrated in vacuo. The residue was crystallized from methylene chloride-hexane to yield 1.87 g (87% yield), melting point 61°-66°, of 4-[4-acetyl-3-[[5-(4-acetyl-3-hydroxy-2-propylphenoxy)pentyl]oxy]-2-propylphenoxy]butanoic acid.

EXAMPLE 56

Preparation of
[4-acetyl-3-[3-(3-bromopropoxy)propoxy]-2-propyl-phenoxy]acetic acid ethyl ester A mixture of 2.5 g (0.0089 mole) of (4-acetyl-3-hydroxy-2-propylphenoxy)acetic acid ethyl ester, 11.6 g (0.045 mole) of 3,3'-dibromodipropyl ether, 1.0 g (0.0072 mole) of potassium carbonate in 50 ml of anhydrous acetone and 25 ml of anhydrous dimethylformamide was stirred at reflux for 66 hours. Additional 1.0 g portions of potassium carbonate were added after 6,18,26 and 42 hours. The reaction mixture was filtered and the filtrate was concentrated in vacuo to yield an oil which was chromatographed on 125 g of silica gel. Elution with 10% ethyl acetate-toluene gave 1.9 g (47% yield) of [4-acetyl-3-[3-(3-bromopropoxy)propoxy]-2-propylphenoxy]acetic acid ethyl ester as an oil.

EXAMPLE 57

Preparation of
[4-acetyl-3-[3-[3-(4-acetyl-3-hydroxy-2-propylphenoxy)propoxy]propoxy]-2-propylphenoxy]acetic acid ethyl ester A mixture of 1.89 g (0.004 mole) of [4-acetyl-3-[3-(3-bromopropoxy)propoxy]-2-propylphenoxy]acetic acid ethyl ester, 0.80 g (0.004 mole) of 1-(2,4-dihydroxy-3-propylphenyl)ethanone, and 1.14 g (0.0082 mole) of potassium carbonate in 40 ml of anhydrous acetone and 20 ml of anhydrous dimethylformamide was stirred at reflux for 20 hours. The solvents were removed in vacuo and the residue was purified by HPLC using 35% ethyl acetate-hexane to give 1.69 g (72% yield) of [4-acetyl-3-[3-[3-(4-acetyl-3-hydroxy-2-propylphenoxy)-propoxy]propoxy]-2-propylphenoxy]acetic acid ethyl ester as an oil.

EXAMPLE 58

Preparation of
[4-Acetyl-3-[3-[3-(4-acetyl-3-hydroxy-2-propylphenoxy)propoxy]propoxy]-2-propylphenoxy]acetic acid.

A solution of 1.65 g (0.0029 mole) of [4-acetyl-3-[3-[3-(4-acetyl-3-hydroxy-2-propylphenoxy)propoxy]propoxy]-2-propylphenoxy]acetic acid ethyl ester in 50 ml of methanol and 14.4 ml (0.014 mole) of 1.0N sodium hydroxide was stirred at reflux for 2 hours. Most of the solvent was removed in vacuo and the pH of the residue was adjusted to 2.0. The product was extracted with methylene chloride and the dried (magnesium sulfate) extract was concentrated in vacuo to an oil which was crystallized from ether-hexane to give 1.28 g (81% yield), melting point 86°–90°, of [4-acetyl-3-[3-[3-(4-acetyl-3-hydroxy-2-propylphenoxy)propoxy]propoxy]-2-propylphenoxy]acetic acid.

EXAMPLE 59

Preparation of
4-[4-acetyl-3-[3-(3-bromopropoxy)propoxy]-2-propylphenoxy]butanoic acid ethyl ester A mixture of 2.5 g (0.008 mole) of 4-(4-acetyl-3-hydroxy-2-propylphenoxy)butanoic acid ethyl ester, 10.6 g (0.041 mole) of 3,3'-dibromodipropyl ether and 1.0 g (0.0072 mole) of potassium carbonate in 50 ml of anhydrous acetone and 25 ml of anhydrous dimethylformamide was stirred at reflux for 66 hours. Additional 1.0 g portions of potassium carbonate were added at 6, 18, 26 and 42 hours. The reaction mixture was filtered and the filtrate was concentrated in vacuo to yield an oil which was chromatographed on 150 g of silica gel. Elution with 7% ethyl acetate-toluene gave 2.16 g (55% yield) of 4-[4-acetyl-3-[3-(3-bromopropoxy)propoxy]-2-propylphenoxy]butanoic acid ethyl ester as an oil.

EXAMPLE 60

Preparation of
4-[4-acetyl-3-[3-[3-(4-acetyl-3-hydroxy-2-propylphenoxy)propoxy]propoxy]-2-propylphenoxy]butanoic acid ethyl ester A mixture of 2.13 g (0.0044 mole) of 4-[4-acetyl-3-[3-(3-bromopropoxy)propoxy]-2-propylphenoxy]butanoic acid ethyl ester, 0.85 g (0.0044 mole) of 1-(2,4-dihydroxy-3-propylphenyl)ethanone and 1.2 g (0.0087 mole) of potassium carbonate in 40 ml of anhydrous acetone and 20 ml of anhydrous dimethylformamide was stirred at reflux for 20 hours. The solvents were removed in vacuo and the residue was purified by HPLC using 35% ethyl acetate-hexane to give 2.15 g (82% yield) of [4-acetyl-3-[3-[3-(4-acetyl-3-hydroxy-2-propylphenoxy)propoxy]propoxy]-2-propylphenoxy]butanoic acid ethyl ester as an oil.

EXAMPLE 61

Preparation of
4-[4-Acetyl-3-[3-[3-(4-acetyl-3-hydroxy-2-propylphenoxy)propoxy]propoxy]-2-propylphenoxy]butanoic acid A solution of 2.06 g (0.0034 mole) of 4-[4-acetyl-3-[3-[3(4-acetyl-3-hydroxy-2-propylphenoxy)propoxy]propoxy]-2-propylphenoxy]butanoic acid ethyl ester in 50 ml of methanol and 17 ml (0.017 mole) of 1.0N sodium hydroxide was stirred at reflux for 2 hours. Most of the solvent was removed and the pH of the residue was adjusted to 2.0 The product was extracted with methylene chloride. The extract was washed with water, dried (magnesium sulfate) and concentrated in vacuo to give 1.81 g (92% yield) of 4-[4-acetyl-3-[3-[3-(4-acetyl-3-hydroxy-2-propylphenoxy)propoxy]propoxy]-2-propylphenoxy]butanoic acid as an oil.

EXAMPLE 62

Preparation of
[4-Acetyl-3-[4-(4-iodobutoxy)butoxy]-2-propylphenoxy]acetic acid ethyl ester A mixture of 2.5 g (0.0089 mole) of (4-acetyl-3-hydroxy-2-propylphenoxy)acetic acid ethyl ester, 17.0 g (0.0446 mole) of 4,4'-diiododibutyl ether and 1.0 g (0.0072 mole) of anhydrous potassium carbonate in 75 ml of anhydrous acetone was stirred at reflux for 65 hours. Additional 1.0 g portions of potassium carbonate were added at 4, 20, 28 and 44 hours. The reaction mixture was filtered and the filtrate was concentrated in vacuo to a residue which was purified by HPLC using 5% ethyl acetate-toluene to give 2.87 g (61% yield) of [4-acetyl-3-[4-(4-iodobutoxy)butoxy]-2-propylphenoxy]acetic acid ethyl ester as an oil.

EXAMPLE 63

Preparation of
[4-Acetyl-3-[4-[4-(4-acetyl-3-hydroxy-2-propylphenoxy)butoxy]butoxy]-2-propylphenoxy]acetic acid ethyl ester A mixture of 1.00 g (0.0052 mole) of 1-(2,4-dihydroxy-3-propylphenyl)ethanone, 2.78 g (0.0052 mole) of [4-acetyl-3-[4-(4-iodobutoxy)butoxy]-2-propylphenoxy]acetic acid ethyl ester and 1.44 g (0.010 mole) of anhydrous potassium carbonate in 75 ml of anhydrous acetone was stirred at reflux for 18 hours. The reaction mixture was filtered and the filtrate was concentrated in vacuo. The residue was purified by HPLC using 35% ethyl acetate-hexane to give 2.72 g (87% yield) of [4-acetyl-3-[4-[4-(4-acetyl-3-hydroxy-2-propylphenoxy)butoxy]butoxy]-2-propylphenoxy]acetic acid ethyl ester as an oil.

EXAMPLE 64

Preparation of
[4-acetyl-3-[4-[4-(4-acetyl-3-hydroxy-2-propylphenoxy)butoxy]butoxy]-2-propylphenoxy]acetic acid A solution of 2.617 g (0.0044 mole) of [4-acetyl-3-[4-[4-(4-acetyl-3-hydroxy-2-propylphenoxy)butoxy]butoxy]-2-propylphenoxy]acetic acid ethyl ester in 50 ml of methanol and 21.8 ml of 1.0N sodium hydroxide was stirred at reflux for 2 hours. Most of the solvent was removed in vacuo and the pH of the residue was adjusted to 2.0. The product was extracted with methylene chloride and the dried (magnesium sulfate) extract was concentrated in vacuo. The residue was crystallized from ether-hexane to give 2.05 g (82% yield) of [4-acetyl-3-[4-[4-(4-acetyl-3-hydroxy-2-propylphenoxy)butoxy]butoxy]-2-propylphenoxy]acetic acid, melting point 68°–71°.

EXAMPLE 65

Preparation of
[4-acetyl-3-[5-(4-acetyl-6-chloro-3-hydroxy-2-propylphenoxy)pentyloxy]-2-propylphenoxy]acetic acid ethyl ester A mixture of 1.10 g (0.0049 mole) of 1-(5-chloro-2,4-dihydroxy-3-propylphenyl)ethanone, 2.08 g (0.0049 mole) of [4-acetyl-3-[(5-bromopentyl)oxy]-3-propylphenoxy]acetic acid ethyl ester and 1.33 g (0.0097 mole) of potassium carbonate in 40 ml of anhydrous acetone and 20 ml of anhydrous dimethylformamide was stirred at reflux for 22 hours. The reaction mixture was concentrated in vacuo and the residue was purified by HPLC using 25% ethyl acetate-hexane to give 0.96 g (34% yield) of [4-acetyl-3-[5-(4-acetyl-6-chloro-3-hydroxy-2-propylphenoxy)pentyloxy]-2-propylphenoxy]acetic acid ethyl ester as an oil.

EXAMPLE 66

Preparation of
[4-acetyl-3-[5-(4-acetyl-6-chloro-3-hydroxy-2-propylphenoxy)pentyloxy]-2-propylphenoxy]acetic acid A solution of 0.945 g (0.0016 mole) of [4-acetyl-3-[5-(4-acetyl-6-chloro-3-hydroxy-2-propylphenoxy)pentyloxy]-2-propylphenoxy]acetic acid ethyl ester in 50 ml of methanol and 8.2 ml (0.0082 mole) of 1.0N sodium hydroxide was stirred at reflux for 2 hours. Most of the solvent was removed in vacuo and the pH of the residue was adjusted to 2.0. The product was extracted with methylene chloride and the dried (magnesium sulfate) extract was concentrated in vacuo. The residue was crystallized from ether-hexane to give 0.710 g (79% yield) of [4-acetyl-3-[5-(4-acetyl-6-chloro-3-hydroxy-2-propylphenoxy)pentyloxy]-2-propylphenoxy]acetic acid, melting point 77°–80°.

EXAMPLE 67

Preparation of
4-[4-acetyl-3-[5-(4-acetyl-6-chloro-3-hydroxy-2-propylphenoxy)pentyloxy]-2-propylphenoxy]butanoic acid ethyl ester A mixture of 0.990 g (0.0043 mole) of 1-(5-chloro-2,4-dihydroxy-3-propylphenyl)ethanone, 1.980 g (0.0043 mole) of 4-[4-acetyl-3-[(5-bromopentyl)oxy]-3-propylphenoxy]butanoic acid ethyl ester and 1.2 g (0.0087 mole) of anhydrous potassium carbonate in 40 ml of anhydrous acetone and 20 ml of anhydrous dimethylformamide was stirred at reflux for 22 hours. The reaction mixture was concentrated in vacuo and the residue was purified by HPLC using 25% ethyl acetate-hexane to give 1.008 g (38% yield) of 4-[4-acetyl-3-[5-(4-acetyl-6-chloro-3-hydroxy-2-propylphenoxy)pentyloxy]-2-propylphenoxy]butanoic acid ethyl ester as an oil.

EXAMPLE 68

Preparation of
4-[4-acetyl-3-[5-(4-acetyl-6-chloro-3-hydroxy-2-propylphenoxy)pentyloxy]-2-propylphenoxy]butanoic acid A solution of 0.978 g (0.0016 mole) of 4-[4-acetyl-3-[5-(4-acetyl-6-chloro-3-hydroxy-2-propylphenoxy)pentyloxy]-2-propylphenoxy]butanoic acid ethyl ester in 50 ml of methanol and 8.1 ml (0.0081 mole) of 1.0N sodium hydroxide was stirred at reflux for 2 hours. Most of the solvent was removed in vacuo and the pH of the residue was adjusted to 2.0. The product was extracted with methylene chloride and the dried (magnesium sulfate) extract was concentrated in vacuo to give 0.850 g (91% yield) of 4-[4-acetyl-3-[5-(4-acetyl-6-chloro-3-hydroxy-2-propylphenoxy)pentyloxy]-2-propylphenoxy]butanoic acid as an oil.

EXAMPLE 69

Preparation of
4-[4-acetyl-3-[2-[2-[2-[(methylsulfonyl)oxy]ethoxy]ethoxy]ethoxy]-2-propylphenoxy]butanoic acid ethyl ester A mixture of 4.0 g of 4-(4-acetyl-3-hydroxy-2-propylphenoxy)butanoic acid ethyl ester, 19.9 g of triethylene glycol dimesylate and 3.6 g of anhydrous potassium carbonate in 80 ml of anhydrous acetone and 40 ml of anhydrous dimethylformamide was stirred at reflux for 23 hours. The reaction mixture was filtered and the filtrate was concentrated in vacuo to an oil which was purified by high pressure liquid chromatography using 30% ethyl acetate-toluene to give 3.0 g (45% yield) of 4-[4-acetyl-3-[2-[2-[2-[(methylsulfonyl)oxy]ethoxy]ethoxy]ethoxy]-2-propylphenoxy]butanoic acid ethyl ester as an oil.

EXAMPLE 70

Preparation of
4-[4-acetyl-3-[2-[2-[2-(4-acetyl-3-hydroxy-2-propylphenoxy)ethoxy]ethoxy]ethoxy]-2-propylphenoxy]butanoic acid ethyl ester A mixture of 1.100 g of 1-(2,4-dihydroxy-3-propylphenyl)ethanone, 2.939 g of 4-[4-acetyl-3-[2-[2-[2-[(methylsulfonyl)oxy]ethoxy]ethoxy]ethoxy]-2-propylphenoxy]butanoic acid ethyl ester and 1.56 g of anhydrous potassium carbonate in 80 ml of anhydrous acetone and 40 ml of anhydrous dimethylformamide was stirred at reflux for 20 hours. The reaction mixture was filtered and the filtrate was concentrated in vacuo to a dark oil which was purified by high pressure liquid chromatography using 40% ethyl acetatehexane to give 2.413 g (69% yield) of 4-[4-acetyl-3-[2-[2-[2-(4-acetyl-3-hydroxy-2-propylphenoxy)ethoxy]ethoxy]ethoxy]-2-propylphenoxy]butanoic acid ethyl ester as an oil.

EXAMPLE 71

Preparation of
4-[4-acetyl-3-[2-[2-[2-(4-acetyl-3-hydroxy-2-propylphenoxy)ethoxy]ethoxy]ethoxy]-2-propylphenoxy]butanoic acid A solution of 2.313 g of 4-[4-acetyl-3-[2-[2-[2-(4-acetyl-3-hydroxy-2-propylphenoxy)ethoxy]ethoxy]ethoxy]-2-propylphenoxy]butanoic acid ethyl ester and 19 ml of 1.0N sodium hydroxide in 50 ml of methanol was stirred at reflux for 2 hours. Most of the methanol was removed in vacuo and the residue was acidified. The product was extracted with methylene chloride and the dried (magnesium sulfate) extract was concentrated in vacuo to give 2.058 g (93% yield) of 4-[4-acetyl-3-[2-[2-[2-(4-acetyl-3-hydroxy-2-propylphenoxy)ethoxy]ethoxy]ethoxy]-2-propylphenoxy]butanoic acid as a viscous oil.

EXAMPLE 72

Preparation of
4-[4-acetyl-3-[3-[3-(4-acetyl-6-chloro-3-hydroxy-2-propylphenoxy)propoxy]propoxy]-2-propylphenoxy]-butanoic acid ethyl ester A mixture of 0.850 g of 1-(5-chloro-2,4-dihydroxy-3-propylphenyl)ethanone, 1.811 g of 4-[4-acetyl-3-[3-(3-bromopropoxy)propoxy]-2-propylphenoxy]butanoic acid ethyl ester and 1.0 g of anhydrous potassium carbonate in 65 ml of anhydrous acetone was stirred at reflux for 4 days. Additional 1.0 g portions of potassium carbonate were added after 21 and 30 hours. The reaction mixture was filtered and the filtrate was concentrated in vacuo to a brown oil. Purification by high pressure liquid chromatography using 20% ethyl acetate-hexane gave 0.516 g (22% yield) of 4-[4-acetyl-3-[3-[3-(4-acetyl-6-chloro-3-hydroxy-2-propylphenoxy)propoxy]propoxy]-2-propylphenoxy]butanoic acid ethyl ester as a yellow oil.

EXAMPLE 73

Preparation of
4-[4-acetyl-3-[3-[3-(4-acetyl-6-chloro-3-hydroxy-2-propylphenoxy)propoxy]propoxy]-2-propylphenoxy]-butanoic acid A solution of 0.506 g of 4-[4-acetyl-3-[3-[3-(4-acetyl-6-chloro-3-hydroxy-2-propylphenoxy)propoxy]propoxy]-2-propylphenoxy]butanoic acid ethyl ester in 4.0 ml of 1.0N sodium hydroxide and 20 ml of methanol was stirred at reflux for 2 hours. The methanol was removed in vacuo and the residue was acidified. The product was extracted with ethyl acetate and the dried (magnesium sulfate) extract was concentrated in vacuo to give 0.461 g (95% yield) of 4-[4-acetyl-3-[3-[3-(4-acetyl-6-chloro-3-hydroxy-2-propylphenoxy)propoxy]propoxy]-2-propylphenoxy]butanoic acid as an oil.

EXAMPLE 74

Preparation of
4-[4-acetyl-3-[2-[2-[2-(2-bromoethoxy)ethoxy]ethoxy]ethoxy]-2-propylphenoxy]butanoic acid ethyl ester A mixture of 3.08 g of 4-(4-acetyl-3-hydroxy-2-propylphenoxy)butanoic acid ethyl ester, 16.0 g of 1,11-dibromo-3,6,9-trioxaundecane and 2.8 g of anhydrous potassium carbonate in 75 ml of anhydrous acetone was stirred at reflux for 5 days. During this period, 1.0 g portions of potassium carbonate were added after 18 hours and after 25 hours. The reaction mixture was filtered and the filtrate was concentrated in vacuo to an oil (20 g) which was chromatographed on 200 g of silica gel using 10% ethyl acetatetoluene to give 3.24 g (59% yield) of 4-[4-acetyl-3-[2-[2-[2-(2-bromoethoxy)ethoxy]ethoxy]ethoxy]-2-propylphenoxy]butanoic acid ethyl ester as an oil.

EXAMPLE 75

Preparation of
4-[4-acetyl-3-[2-[2-[2-[2-(4-acetyl-3-hydroxy-2-propylphenoxy)ethoxy]ethoxy]ethoxy]ethoxy]-2-propylphenoxy]butanoic acid ethyl ester A mixture of 0.9500 g of 1-(2,4-dihydroxy-3-propylphenyl)ethanone, 2.677 g of 4-[4-acetyl-3-[2-[2-[2-(2-bromoethoxy)ethoxy]ethoxy]ethoxy]-2-propylphenoxy]butanoic acid ethyl ester and 1.0 g of anhydrous potassium carbonate in 40 ml of anhydrous acetone was stirred at reflux for 17 hours. An additional 1.0 g of potassium carbonate was added and reflux was continued for 25 hours. The reaction mixture was filtered and the filtrate was concentrated in vacuo to an oil which was chromatographed on 200 g of silica gel. Elution with 30% ethyl acetate-toluene gave 2.3 g (71% yield) of 4-[4-acetyl-3-[2-[2-[2-[2-(4-acetyl-3-hydroxy-2-propylphenoxy)ethoxy]ethoxy]ethoxy]ethoxy]-2-propylphenoxy]butanoic acid ethyl ester as an oil.

EXAMPLE 76

Preparation of
4-[4-acetyl-3-[2-[2-[2-[2-(4-acetyl-3-hydroxy-2-propylphenoxy)ethoxy]ethoxy]ethoxy]ethoxy]-2-propylphenoxy]butanoic acid A solution of 2.30 g of 4-[4-acetyl-3-[2-[2-[2-[2-(4-acetyl-3-hydroxy-2-propylphenoxy)ethoxy]ethoxy]ethoxy]ethoxy]-2-propylphenoxy]butanoic acid ethyl ester in 17 ml of 1.0N sodium hydroxide and 50 ml of methanol was stirred at reflux for 7 hours. The methanol was removed in vacuo and the residue was acidified. The product was extracted with ether and the dried (magnesium sulfate) extract was concentrated in vacuo to an oil (2.40 g). Chromatography on 150 g of silica gel and elution with a solvent mixture of 5% acetic acid: 70% toluene: 25% ethyl acetate gave 1.72 g (78% yield) of 4-[4-acetyl-3-[2-[2-[2-[2-(4-acetyl-3-hydroxy-2-propylphenoxy)ethoxy]ethoxy]ethoxy]ethoxy]-2-propylphenoxy]butanoic acid as a viscous oil.

EXAMPLE 77

Preparation of
4-[4-acetyl-3-[4-(4-iodobutoxy)butoxy]-2-propylphenoxy]butanoic acid ethyl ester A mixture of 3.08 g of 4-(4-acetyl-3-hydroxy-2-propylphenoxy)butanoic acid ethyl ester, 19.0 g of 4,4'-diiododibutyl ether and 2.0 g of anhydrous potassium carbonate in 75 ml of anhydrous acetone was stirred at reflux for 6 days. Additional 1.0 g portions of potassium carbonate were added during this period after 17, 39 and 46 hours. The reaction mixture was filtered and the filtrate was concentrated in vacuo to an oil. Chromatography on 200 g of silica gel and elution with 10% ethyl acetate-toluene gave 3.00 g (53% yield) of 4-[4-acetyl-3-[4-(4-iodobutoxy)butoxy]-2-propylphenoxy]butanoic acid ethyl ester as an oil.

EXAMPLE 78

Preparation of
4-[4-acetyl-3-[4-[4-(4-acetyl-3-hydroxy-2-propylphenoxy)butoxy]butoxy]-2-propylphenoxy]butanoic acid ethyl ester A mixture of 0.871 g of 1-(2,4-dihydroxy-3-propylphenyl)ethanone, 2.536 g of 4-[4-acetyl-3-[4-(4-iodobutoxy)butoxy]-2-propylphenoxy]butanoic acid ethyl ester and 0.94 g of anhydrous potassium carbonate in 40 ml of anhydrous acetone was stirred at reflux for 17 hours. An additional 1.0 g of potassium carbonate was added and reflux was continued for 25 hours. The reaction mixture was filtered and the filtrate was concentrated in vacuo to an oil which was chromatographed on 200 g of silica gel. Elution with 20% ethyl acetate-toluene gave 2.71 g (96% yield) of 4-[4-acetyl-3-[4-[4-(4-acetyl-3-hydroxy-2-propylphenoxy)butoxy]butoxy]-2-propylphenoxy]butanoic acid ethyl ester as an oil.

EXAMPLE 79

Preparation of 4-[4-acetyl-3-[4-[4-(4-acetyl-3-hydroxy-2-propylphenoxy)butoxy]butoxy]-2-propylphenoxy]butanoic acid A solution of 2.71 g of 4-[4-acetyl-3-[4-[4-(4-acetyl-3-hydroxy-2-propylphenoxy)butoxy]butoxy]-2-propylphenoxy]butanoic acid ethyl ester in 20 ml of 1.0N sodium hydroxide and 90 ml of methanol was stirred at reflux for 6.5 hours. The methanol was removed in vacuo and the residue was acidified. The product was extracted with ether and the dried (magnesium sulfate) extract was concentrated in vacuo to an oil. Chromatography on 150 g of silica gel and elution with a solvent mixture of 5% acetic acid: 70% toluene: 25% ethyl acetate gave 2.32 g (90% yield) of 4-[4-acetyl-3-[4-[4-(4-acetyl-3-hydroxy-2-propylphenoxy)butoxy]butoxy]-2-propylphenoxy]butanoic acid as an oil.

EXAMPLE 80

CAPSULE FORMULATION

| Ingredients | mg/capsule | | | |
| --- | --- | --- | --- | --- |
|  | 25 mg | 50 mg | 100 mg | 200 mg |
| [4-acetyl-3-[3-(4-acetyl-3-hydroxy-2-propylphenoxy)propoxy]-2-propylphenoxy]acetic acid | 25 | 50 | 100 | 200 |
| Lactose | 375 | 155 | 200 | 140 |
| Starch | 30 | 30 | 35 | 40 |
| Talc | 20 | 15 | 15 | 20 |
| Weight of capsule | 450 mg | 250 mg | 350 mg | 400 mg |

Procedure:

Mill [4-acetyl-3-[3-(4-acetyl-3-hydroxy-2-propylphenoxy)propoxy]-2-propylphenoxy]acetic acid, lactose and starch in a suitable mixer. Mill. Add talc and mix well. Encapsulate on suitable equipment.

EXAMPLE 81

TABLET FORMULATION (Wet granulation)

| Ingredients | mg/tablet | | | |
| --- | --- | --- | --- | --- |
|  | 25 mg | 50 mg | 100 mg | 200 mg |
| [4-acetyl-3-[3-(4-acetyl-3-hydroxy-2-propylphenoxy)propoxy]-2-propylphenoxy]acetic acid | 25 | 50 | 100 | 200 |
| Lactose | 280 | 153 | 187 | 171 |
| Modified Starch | 55 | 25 | 35 | 45 |
| Pregelatinized Starch | 35 | 20 | 25 | 30 |
| Distilled water q.s. | — | — | — | — |
| Magnesium Stearate | 5 | 2 | 3 | 4 |
| Weight of tablet | 400 mg | 250 mg | 350 mg | 450 mg |

Procedure:

Mix, [4-acetyl-3-[3-(4-acetyl-3-hydroxy-2-propylphenoxy)propoxy]-2-propylphenoxy]acetic acid, lactose, modified starch and pregelatinized starch in a suitable mixer. Granulate with sufficient distilled water to proper consistency. Mill. Dry in a suitable oven. Mill and mix with magnesium stearate for 3 minutes. Compress on a suitable press equipped with appropriate punches.

EXAMPLE 82

TABLET FORMULATION (Direct Compression)

| Ingredients | mg/tablet 25 mg |
| --- | --- |
| [4-acetyl-3-[3-(4-acetyl-3-hydroxy-2-propylphenoxy)propoxy]-2-propylphenoxy]acetic acid | 25 |
| Lactose | 181 |
| Avicel | 55 |
| Direct Compression Starch | 35 |
| Magnesium Stearate | 4 |
| Weight of tablet | 300 mg |

Procedure

Mix [4-acetyl-3-[3-(4-acetyl-3-hydroxy-2-propylphenoxy)propoxy]-2-propylphenoxy]acetic acid with an equal amount of lactose. Mix well. Mix with avicel and direct compression starch, and the remaining amount of lactose. Mix well. Add magnesium stearate and mix for 3 minutes. Compression on a suitable press equipped with appropriate punches.

We claim:

1. A compound of the formula

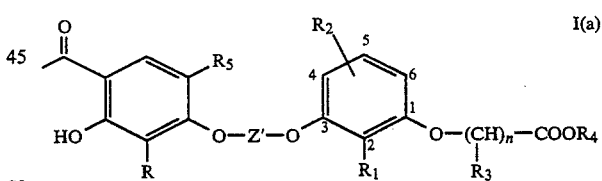

I(a)

wherein R is hydrogen or lower alkyl, $R_1$ is hydrogen or lower alkyl, $R_2$ is lower alkanoyl, $R_3$ is hydrogen or methyl, $R_4$ is hydrogen or lower alkyl, $R_5$ is hydrogen, halogen, lower alkyl or lower alkanoyl, $Z^1$ is lower alkylene or 2-hydroxypropylene, and n is an integer from 1 to 7, or, when $R_4$ is hydrogen, a salt thereof with a pharmaceutically acceptable base.

2. A compound in accordance with claim 1, wherein $R_2$ is in the 4-position.

3. A compound in accordance with claim 2, wherein R and $R_1$ are lower alkyl, $R_3$ and $R_5$ are hydrogen, and n is 1 or 3.

4. A compound in accordance with claim 3, wherein R and $R_1$ are propyl, $R_2$ is acetyl, and $Z'$ is propylene or pentylene.

5. A compound in accordance with claim 4, wherein $R_4$ is hydrogen.

6. A compound in accordance with claim 1, [4-acetyl-3-[3-(4-acetyl-3-hydroxy-2-propylphenoxy)propoxy]-2-propylphenoxy]acetic acid.

7. A compound in accordance with claim 1, racemic [4-acetyl-3-[3-(4-acetyl-3-hydroxy-2-propylphenoxy)-2-hydroxypropoxy]-2-propylphenoxy]acetic acid.

8. A compound in accordance with claim 1, 4-[4-acetyl-3-[3-(4-acetyl-3-hydroxy-2-propylphenoxy)propoxy]-2-propylphenoxy]butanoic acid.

9. A compound in accordance with claim 1, [4-acetyl-3-[5-(4-acetyl-3-hydroxy-2-propylphenoxy)pentyloxy]-2-propylphenoxy]acetic acid.

10. A compound in accordance with claim 1, [4-Acetyl-3-[3-(4-acetyl-6-chloro-3-hydroxy-2-propylphenoxy)propoxy]-2-propylphenoxy]acetic acid.

11. A compound in accordance with claim 1, 4-[4-acetyl-3-[[5-(4-acetyl-3-hydroxy-2-propylphenoxy)pentyl]oxy]-2-propylphenoxy]butanoic acid.

12. A pharmaceutical composition comprising a compound of the formula

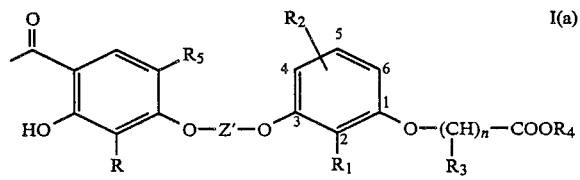

wherein R is hydrogen or lower alkyl, $R_1$ is hydrogen or lower alkyl, $R_2$ is lower alkanoyl, $R_3$ is hydrogen or methyl, $R_4$ is hydrogen or lower alkyl, $R_5$ is hydrogen, halogen, lower alkyl or lower alkanoyl, $Z^1$ is lower alkylene or 2-hydroxypropylene, and n is an integer from 1 to 7, or, when $R_4$ is hydrogen, a salt thereof with a pharmaceutically acceptable base, and an inert carrier material.

13. A pharmaceutical composition in accordance with claim 12, wherein the compound of formula Ia is 4-[4-acetyl-3-[[5-(4-acetyl-3-hydroxy-2-propylphenoxy)pentyl]oxy]-2-propylphenoxy]butanoic acid.

14. A method of treating allergic conditions which comprises administering a therapeutically effective amount of a compound of the formula

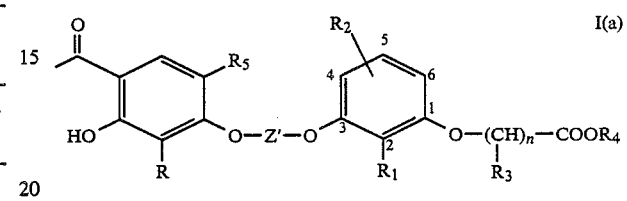

wherein R is hydrogen or lower alkyl, $R_1$ is hydrogen or lower alkyl, $R_2$ is lower alkanoyl, $R_3$ is hydrogen or methyl, $R_4$ is hydrogen or lower alkyl, $R_5$ is hydrogen, halogen, lower alkyl or lower alkanoyl, $Z^1$ is lower alkylene or 2-hydroxypropylene and n is an integer from 1 to 7, or, when $R_4$ is hydrogen, a salt thereof with a pharmaceutically acceptable base.

15. A method in accordance with claim 14, wherein the compound of formula Ia is 4-[4-acetyl-3-[[5-(4-acetyl-3-hydroxy-2-propylphenoxy)pentyl]oxy]-2-propylphenoxy]butanoic acid.

* * * * *